US 7,859,656 B2
(12) United States Patent
Uto et al.

(10) Patent No.: US 7,859,656 B2
(45) Date of Patent: Dec. 28, 2010

(54) DEFECT INSPECTION METHOD AND SYSTEM

(75) Inventors: Sachio Uto, Yokohama (JP); Hiroyuki Nakano, Chigasaki (JP); Yukihiro Shibata, Fujisawa (JP); Akira Hamamatsu, Yokohama (JP); Yuta Urano, Yokohama (JP)

(73) Assignee: Hitachi high-Technologies Corporation, Tokyo (JP)

( * ) Notice: Subject to any disclaimer, the term of this patent is extended or adjusted under 35 U.S.C. 154(b) by 0 days.

(21) Appl. No.: 12/366,956

(22) Filed: Feb. 6, 2009

(65) Prior Publication Data

US 2009/0141269 A1 Jun. 4, 2009

Related U.S. Application Data

(63) Continuation of application No. 11/626,925, filed on Jan. 25, 2007, now Pat. No. 7,492,452.

(30) Foreign Application Priority Data

Mar. 1, 2006 (JP) ............................. 2006-054289

(51) Int. Cl.
*G01N 21/00* (2006.01)
*G01N 21/88* (2006.01)
*H01L 27/00* (2006.01)

(52) U.S. Cl. ............. 356/237.2; 356/237.4; 356/237.5; 250/548

(58) Field of Classification Search ... 356/237.1–237.6, 356/394; 250/559.4, 559.41, 559.45, 208.1, 250/548; 382/141, 145
See application file for complete search history.

(56) References Cited

U.S. PATENT DOCUMENTS 3,814,945 A * 6/1974 Allnutt et al. .......... 250/559.49

(Continued)

FOREIGN PATENT DOCUMENTS

JP 62-089336 4/1987

(Continued)

*Primary Examiner*—Sang Nguyen
(74) *Attorney, Agent, or Firm*—Antonelli, Terry, Stout & Kraus, LLP.

(57) ABSTRACT

An inspection system includes: a facility that uses wide-band illumination light having different wavelengths and single-wavelength light to perform dark-field illumination on an object of inspection, which has the surface thereof coated with a transparent film, in a plurality of illuminating directions at a plurality of illuminating angles; a facility that detects light reflected or scattered from repetitive patterns and light reflected or scattered from non-repetitive patterns with the wavelengths thereof separated from each other; a facility that efficiently detects light reflected or scattered from a foreign matter or defect in the repetitive patterns or non-repetitive patterns or a foreign matter or defect on the surface of the transparent film; and a facility that removes light, which is diffracted by the repetitive patterns, from a diffracted light image of actual patterns or design data representing patterns. Consequently, a more microscopic defect can be detected stably.

18 Claims, 16 Drawing Sheets

U.S. PATENT DOCUMENTS

| | | | |
|---|---|---|---|
| 4,863,268 A * | 9/1989 | Clarke et al. | 356/237.2 |
| 4,877,326 A | 10/1989 | Chadwick | |
| 4,895,446 A | 1/1990 | Maldari | |
| 6,104,481 A * | 8/2000 | Sekine et al. | 356/237.5 |
| 6,363,166 B1 | 3/2002 | Wihl | |
| 6,621,568 B1 | 9/2003 | Yonezawa | |
| 6,774,987 B2 | 8/2004 | Komatsu | |
| 6,836,560 B2 | 12/2004 | Emery | |
| 6,958,846 B2 | 10/2005 | Huibers | |
| 7,072,034 B2 | 7/2006 | Rosengaus | |
| 7,180,586 B2 | 2/2007 | Neumann | |
| 7,245,364 B2 * | 7/2007 | Moriya | 356/237.1 |
| 7,292,330 B2 | 11/2007 | Saunders | |
| 7,369,223 B2 * | 5/2008 | Hamamatsu et al. | 356/237.2 |
| 7,465,935 B2 * | 12/2008 | Urano et al. | 250/372 |
| 7,492,452 B2 * | 2/2009 | Uto et al. | 356/237.2 |
| 7,528,942 B2 * | 5/2009 | Nakano et al. | 356/237.3 |
| 7,672,799 B2 * | 3/2010 | Shimura et al. | 702/81 |

FOREIGN PATENT DOCUMENTS

| | | |
|---|---|---|
| JP | 63-135848 | 6/1988 |
| JP | 01-117024 | 5/1989 |
| JP | 01-250847 | 10/1989 |
| JP | 10-221267 | 8/1998 |
| JP | 2000-105203 | 4/2000 |
| JP | 2001-060607 | 3/2001 |

* cited by examiner (a)

(b)

(c)

(a)

(b)

(c)

(a)

(b)

(c)

(a)

(b)

(a)

(b)

(a)

(b)

(c)

(d)

(a)

⋮⋮: P-POLARIZED LIGHT
⋯: S-POLARIZED LIGHT
⁙: P+S
○: ELLIPTICALLY POLARIZED LIGHT (b)

(c)

(a)

||| : P-POLARIZED LIGHT
••• : S-POLARIZED LIGHT
||| : P+S
0 : ELLIPTICALLY POLARIZED LIGHT (b)

DEFECT INSPECTION METHOD AND SYSTEM

CROSS REFERENCE TO RELATED APPLICATION

This application is a continuation of U.S. application Ser. No. 11/626,925, filed Jan. 25, 2007 now U.S. Pat. No. 7,492,452, the contents of which are incorporated herein by reference.

BACKGROUND OF THE INVENTION

1. Field of the Invention

The present invention relates to a method and system for inspecting the occurrence of a foreign matter or defect in a device manufacturing process, wherein a foreign matter existent on a thin-film substrate, a semiconductor substrate, or a photomask, or a defect occurring in circuit patterns is detected in the course of manufacturing a semiconductor chip or a liquid crystal product, and the detected foreign matter or defect is analyzed in order to take measures.

2. Description of the Related Art

In a semiconductor manufacturing process, the presence of a foreign matter on a semiconductor substrate (wafer) causes a defective such as imperfect insulation of wiring or a short circuit thereof. Furthermore, due to the trend of semiconductor devices to a more and more microscopic structure, a more microscopic foreign mater brings about imperfect insulation of a capacitor or destruction of a gate oxide film. The foreign matters are mixed in various states because of various causes. Namely, the foreign matters may be produced by a movable unit included in transportation equipment or a human body, produced in processing equipment due to reaction of a process gas or the like, or originally mixed in a chemical agent or material.

Likewise, in a process of manufacturing a liquid crystal display device, if a defective pattern is produced in a work due to a foreign matter, the work cannot be adopted as a display device. The same applies to a manufacturing process of a printed circuit board. The mixture of a foreign matter causes a short circuit or a defective connection in patterns. Under such a background, in the case of semiconductor manufacturing, a plurality of foreign matter inspection systems may be disposed relative to each production line. Thus, the presence of a foreign matter is discovered in the earliest possible stage and fed back to the manufacturing process, whereby a yield in manufacturing of a semiconductor device is improved.

As one of techniques for detecting a foreign matter on a semiconductor substrate, Japanese Unexamined Patent Publication No. 62-89336 (Prior Art 1) has disclosed a method capable of highly sensitively and highly reliably inspecting the presence of a foreign matter and the occurrence of a defect by discarding false or misleading information acquired from patterns. According to the method, light scattered from a foreign matter, which adheres to a semiconductor substrate, after laser light is irradiated to the semiconductor substrate is detected, and then compared with a result of inspection conducted on a semiconductor substrate of the same type that has been inspected immediately previously. Moreover, as disclosed in Japanese Unexamined Patent Publication No. 63-135848 (Prior Art 2), a method is known in which light scattered from a foreign matter, which adheres to a semiconductor substrate, after laser light is irradiated to the semiconductor substrate is detected, and the detected foreign matter is analyzed using an analyzing technique such as laser photoluminescence or secondary X-ray analysis (XMR).

Moreover, disclosed as a technique for inspecting the presence of a foreign matter is a method for irradiating coherent light to a wafer, removing light, which is emitted from repetitive patterns on the wafer, using a spatial filter, and intensifying light reflected from a foreign matter or defect, which lacks repetitiveness, so as to detect the foreign matter or defect. Moreover, a foreign matter inspection system that irradiates light to a major group of straight lines, which is included in circuit patterns formed on a wafer, at an angle of 45°, for fear light having undergone zero-order diffraction due to the major group of straight lines may enter an aperture for an objective lens is described in Japanese Unexamined Patent Publication No. 1-117024 (Prior Art 3). In the Prior Art 3, a spatial filter is used to intercept light reflected from a group of straight lines other than the major group of straight lines.

As prior arts concerning a defect inspection system and method for inspecting a foreign matter or the like, methods described in Japanese Unexamined Patent Publications Nos. 1-250847 (Prior Art 4) and 2000-105203 (Prior Art 5) are known. In particular, as for the Prior Art 5, the patent publication describes that detective optical systems are switched in order to change detectable pixel sizes. As for technologies for measuring the size of a foreign matter, a method is disclosed in Japanese Unexamined Patent Publication No. 2001-60607 (Prior Art 6).

SUMMARY OF THE INVENTION

However, the foregoing Prior Arts 1 to 5 cannot readily, highly sensitively, and quickly detect a microscopic foreign matter or defect on a substance on which repetitive patterns or non-repetitive patterns coexist. Namely, the Prior Arts 1 to 5 are disadvantageous in a point that detective sensitivity (a minimum dimension of a foreign matter to be detected) is low except that for the repetitive patterns such as those realizing memory cells or the like. Moreover, the Prior Arts 1 to 5 are disadvantageous in a point that the detective sensitivity is low relative to a microscopic foreign matter or defect of about 0.1 µm in a diameter existing in a highly densely patterned area. Moreover, the Prior Arts 1 to 5 are disadvantageous in a point that the detective sensitivity is low relative to a foreign matter or defect which causes a short circuit of wiring, or a foreign matter shaped like a thin film. Moreover, the Prior Art 6 is disadvantageous in a point that the precision in measurement of a foreign matter or defect is low. Moreover, the Prior Art 6 is disadvantageous in a point that the detective sensitivity is low relative to a foreign matter on the surface of a wafer coated with a transparent thin film.

The present invention addresses the foregoing problems. An object of the present invention is to provide a defect inspection method and system capable of inspecting an object of inspection on which repetitive patterns and non-repetitive patterns coexist so as to detect a microscopic foreign matter or defect quickly and highly precisely. In particular, the present invention provides a defect inspection method and system capable of stably detecting a microscopic foreign matter or defect while minimizing a difference in sensitivity between inspective areas, that is, a memory unit that includes many repetitive patterns and a logic unit in which non-repetitive patterns exist.

Moreover, another object of the present invention is to provide a defect inspection method and system that are attempted to improve the sensitivity in detecting a defect in a memory unit including many repetitive patterns. Herein, when a setting is designated for intercepting light, which is diffracted by patterns formed on a substrate to be inspected, at a position of a Fourier transform in a detective optical system using a spatial filter, the setting may be designated by employing either light diffracted by actual patterns or design data representing patterns. The setting of the spatial filter is designated prior to inspection of each of a plurality of memory units included in the same die. When each of the memory units is inspected, the setting of the spatial filter is automatically designated in order to highly sensitively detect a microscopic foreign matter or defect in the memory unit.

To be more specific, in one aspect of the present invention, there is provided a defect inspection system including: an illuminative optical system capable of irradiating illuminating luminous fluxes, which are emitted from an illuminative light source and have different wavelengths, to the surface of a substrate to be inspected in mutually different directions and at mutually different tilt angles; an objective lens on which light reflected or scattered from a defect on the substrate to be inspected is converged; a detective optical system realized with an image-formation optical system that separates the wavelengths of the reflected or scattered light converged on the objective lens from one another, and causes the different wavelength components to form images on the light receiving surfaces of respective photodetectors; and a signal processing system that converts image signals produced by the respective photodetectors included in the detective optical system into digital image signals, and detects the defect on the basis of the digital image signals produced by the converter.

In another aspect of the present invention, the detective optical system included in the defect inspection system includes a mechanical unit that varies an image-formation power by keeping constant the relative distances between a Fourier-transform image, which is formed between the objective lens and the image formation optical system, and the substrate to be inspected and photodetectors.

In another aspect of the present invention, the detective optical system included in the defect inspection system includes a spatial filter that is interposed between the objective lens and image formation optical system and that has the ability to intercept light of a specific wavelength out of the light reflected or scattered from the substrate to be inspected. Moreover, according to the present invention, the defect inspection system includes an arrangement that designates the conditions for the spatial filter, which is included in the detective optical system and interposed between the objective lens and image formation optical system, on the basis of design data representing patterns.

In another aspect of the present invention, there is provided a defect inspection system including: an illuminative optical system capable of irradiating an illuminating luminous flux, which is emitted from an illumination light source, to the surface of a substrate to be inspected at a high tilt angle and a low tilt angle that can be switched; a detective optical system including an objective lens which is disposed in a direction optimal for detecting a foreign matter or defect on the object of inspection and on which light reflected or scattered from the foreign mater or defect is converged, an image formation optical system that causes the reflected or scattered light, which is converted on the objective lens, to form an image, and a photodetector that converts the reflected or scattered light, which is caused to form an image by the image formation optical system, into a signal; an A/D converter that when the illuminative optical system illuminates the substrate to be inspected at the high and low tilt angles, converts an image signal produced by the photodetector included in the detective optical system into a digital image signal; a defect detection unit that detects the defect on the basis of the digital image signal produced by the A/D converter; and a means for verifying the detected foreign matter.

In another aspect of the present invention, there is employed a pulsed laser, which emits light that falls within the ultraviolet region, as a low-angle illumination light source. Moreover, one pulse of laser light emitted from the pulsed laser light source is split into a plurality of pulses in order to decrease the peak value of the laser light. The resultant laser light is irradiated to a specimen, whereby the damage the specimen incurs is reduced.

The aforesaid and other objects of the present invention and the features and advantages thereof will be apparent from the following more particular description of preferred embodiments of the invention illustrated in the accompanying drawings.

DESCRIPTION OF THE PREFERRED EMBODIMENTS

Figure 1:
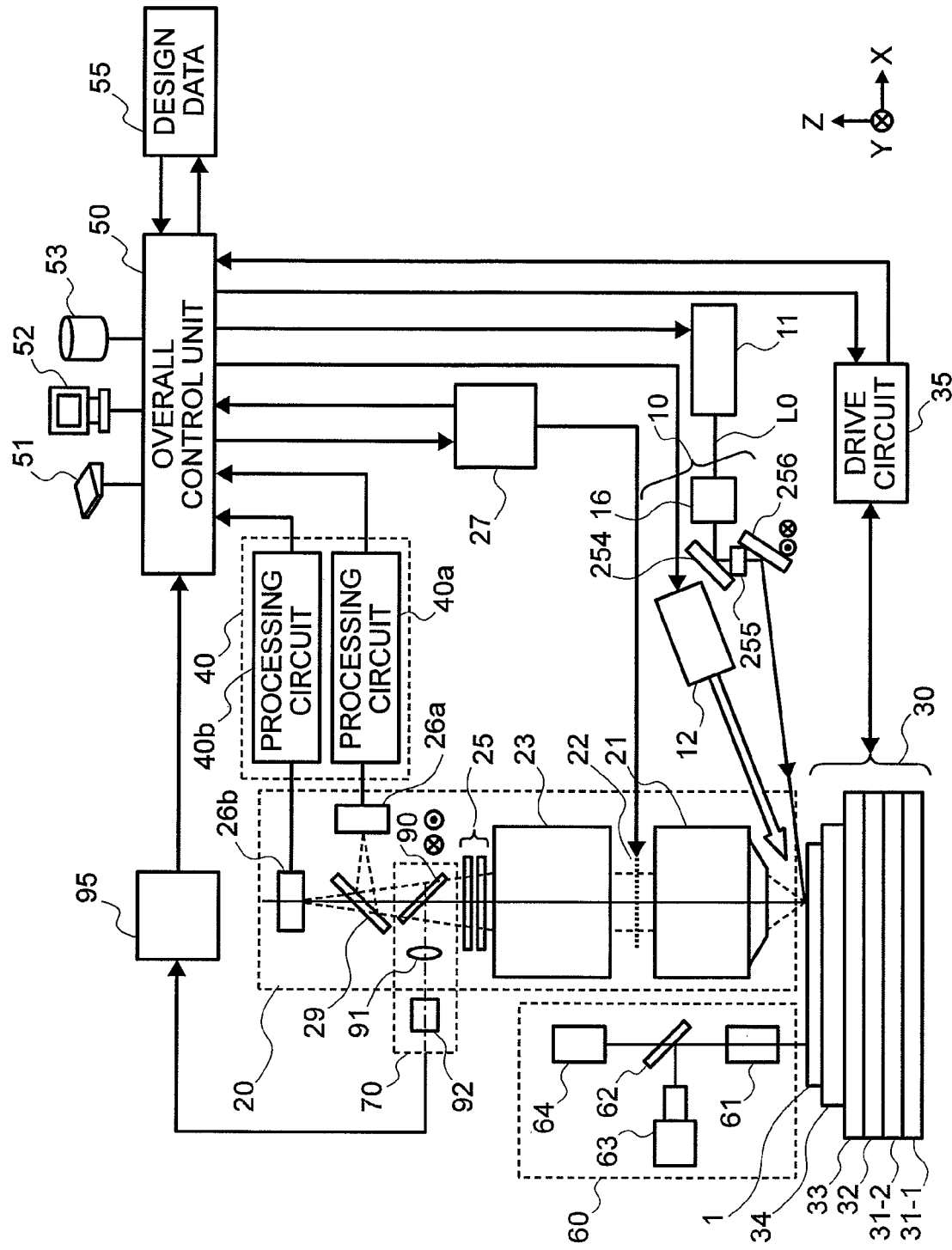
FIG. 1 is a block diagram schematically showing the configuration of a defect inspection system in accordance with the first embodiment.

Referring to the drawings, embodiments of the present invention will be described below.

A defect inspection system in accordance with the present invention highly sensitively and quickly inspects the presence of various defects including a foreign matter, a defective pattern, and a micro-scratch on a substrate to be inspected such as a wafer that is made of various materials through various manufacturing steps, and especially stably detects a defect on the surface of a thin film coated over the surface of the wafer independently of a defect in the thin film.

Figure 2:
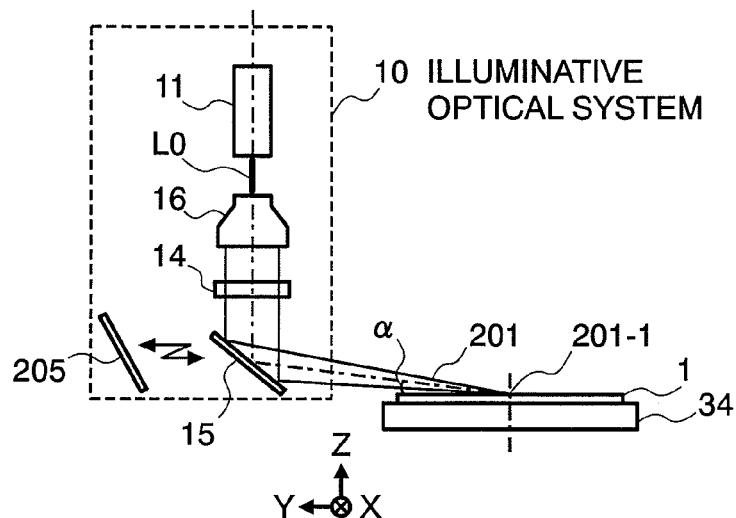
FIG. 2A is a side view for use in explaining the disposition of an illuminative optical system shown in FIG. 1.
FIG. 2B is a perspective view schematically showing the elements of a low-angle illumination optical system included in the first embodiment.
Figure 2:
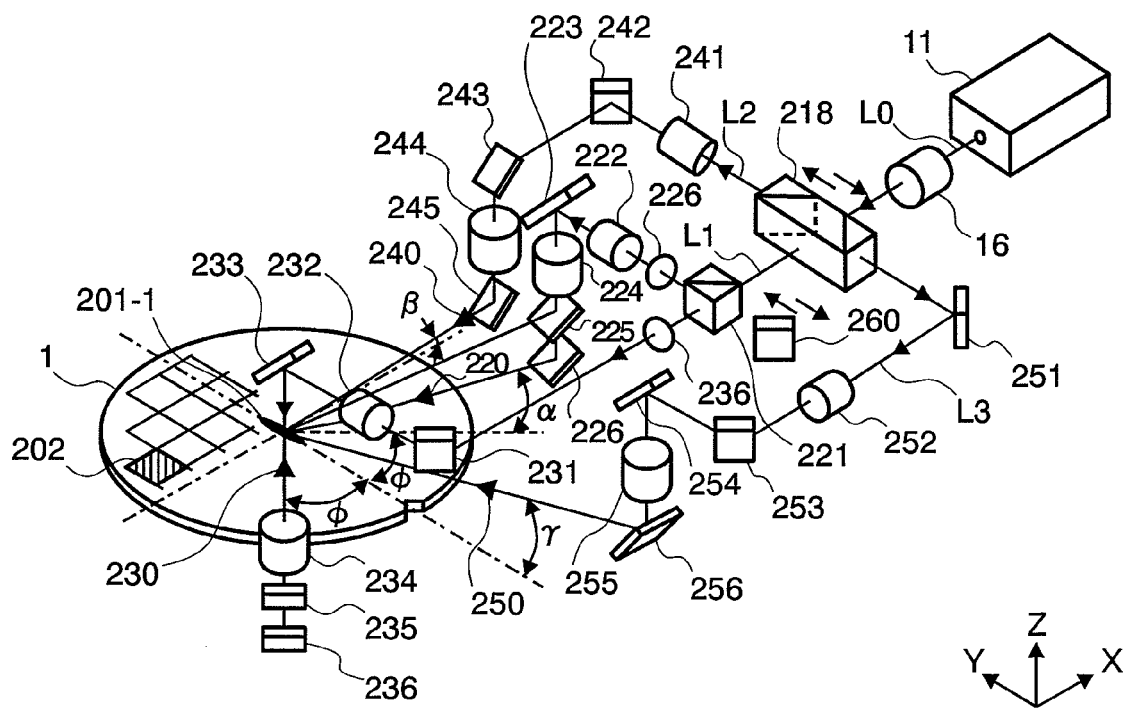
Figure 2:

Specifically, the defect inspection system in accordance with the present invention is designed so that an angle α of irradiation and a direction φ of irradiation at or in which a slit-shaped beam 201 that is, as shown in FIG. 2, produced for illumination by an illuminative optical system 10 can be varied depending on an object of inspection. As shown in FIG. 1, the elements of a detective optical system 20 are arranged so that the surface of the object of inspection and the light receiving surface of a detector 26 will have a relationship of image formation. Moreover, a power for image formation offered by the detective optical system 20 is made variable so that the size of a defect-detected pixel can be determined according to the size of a defect to be detected. Thus, inspection is carried out.

Furthermore, the defect inspection system in accordance with the present invention includes a facility that distinguishes a kind of detected defect by recognizing a difference in light, which is scattered from a defect by irradiating illumination light waves at different angles of irradiation, as a characteristic quantity.

The embodiments of the defect inspection system in accordance with the present invention will be described concretely. The embodiments will be described on the assumption that a defect such as a small or large foreign matter or a micro-scratch on a semiconductor wafer or a transparent film coated over the wafer, a foreign matter in the transparent film, or a defective pattern is inspected. However, the present invention is not limited to the semiconductor wafer but can be applied to a thin-film substrate, a photomask, a thin-film transistor (TFT), or a plasma display panel (PDP).

First Embodiment

FIG. 1 shows the configuration of a defect inspection system in accordance with the first embodiment. The defect inspection system includes mainly an illuminative optical system 10, a variable-power detective optical system 20, a transportation system 30, a signal processing system 40, and an overall control unit 50 that controls the entire defect inspection system.

The transportation system 30 includes an X stage 31-1, a Y stage 21-2, a Z stage 32, and a θ stage 33 that are used to move a placement table bearing a substrate 1 to be inspected such as a wafer that is made of various materials through various manufacturing steps, and a drive circuit 35 that controls the stages.

The illuminative optical system 10 includes an illumination light source 12 whose light falls in a wide wavelength band, a laser light source 11, a beam enlargement optical system 16, mirrors 254 and 256, and a lens 255. Light emitted from the laser light source 11 is enlarged to a certain size by the beam enlargement optical system 16, and then irradiated to the substrate 1 to be inspected in a plurality of oblique directions via the mirror 254, lens 255, and mirror 256.

The detective optical system 20 includes an objective lens 21, a spatial filter 22, an image formation lens 23, an optical filter 25, a beam splitter 29, and photodetectors 26a and 26b such as time-delay integration (TDI) image sensors.

Processing circuits 40a and 40b included in the signal processing system 40 manipulate image signals produced by the photodetectors 26a and 26b respectively so as to detect a defect or foreign matter. The beam splitter 29 reflects light that falls in a specific wavelength band and transmits light having the other wavelengths.

An observational optical system 60 includes a lens 61, a polarization beam splitter 62, an illumination light source 63, and an imaging means 64. Herein, p-polarized light emitted from the illumination light source 63 is reflected from the polarization beam splitter 62, has thus the path thereof angled toward the wafer 1, and is then converged on the lens 61. Consequently, the surface of the wafer 1 is illuminated. Out of light reflected or scattered from the wafer 1, light incident on the lens 61 falls on the polarization beam splitter 62. The s-polarized light component of the light passes through the polarization beam splitter 62, and forms an image which is picked up by the imaging means 64. The wafer 1 is inspected in advance by other inspection system, and the presence or absence of a detected foreign matter and the shape thereof are verified through the observational optical system. Moreover, the observational optical system is used to observe a foreign matter or defect detected by the variable-power detective optical system 20.

The overall control unit 50 designates conditions for inspection or the like, and controls the illuminative optical system 10, variable-power detective optical system 20, transportation system 30, and signal processing system 40. The overall control unit 50 includes an input/output means 51 (including a keyboard and a network), a display means 52, and a memory unit 53. Reference numeral 55 denotes a storage means (server) in which design data including data that represents circuit patterns formed on the surface of the substrate 1 to be inspected is stored. The design data is used to form a spatial optical image.

The defect inspection system includes an automatic focusing control system (not shown) so that an image of the surface of the wafer 1 will be formed on the light receiving surfaces of the respective photodetectors 26a and 26b.

The present inspection system is designed to be able to illuminate the surface of the substrate 1 to be inspected in a plurality of directions. As shown in FIG. 2A, the illuminative optical system 10 includes, as described in the Japanese Unexamined Patent Publication No. 2000-105203, the beam enlargement optical system 16 composed of, for example, a concave lens and a convex lens that are not shown, a lens 14 that reshapes light L0 emitted from the laser light source 11 into a slit-shaped beam, and a mirror 15. The illuminative optical system 10 reshapes the light L0, which is emitted from the laser light source 11, into the slit-shaped beam 201, and irradiates the slit-shaped beam to a slit-shaped area 201-1 on the wafer 1.

The inspection system of the present embodiment includes, as an arrangement for illuminating the surface of the wafer 1 with a single-wavelength laser beam at a low angle (low angle of incidence), an arrangement that irradiates the slit-shaped beam 201 (light irradiated to the slit-shaped area 201-1 on the wafer and referred to as the slit-shaped beam) to the wafer 1 (substrate to be inspected) on the specimen placement table 34 on a planar basis in a plurality of directions (four directions 220, 230, 240, and 250 in FIG. 2B) and at a plurality of illuminating angles (angles α, β, and γ in FIG. 2B).

The reason why illumination light is reshaped into the slit-shaped beam 201 is that an image carried by light that is scattered from a foreign matter or defect under illumination is formed on the detective surfaces of the photodetectors 26 defined by the respective arrays of light receiving elements, and thus detected comprehensively in order to speed up inspection of a foreign matter.

Specifically, the θ stage 33 is driven so that the directions, in which the chips 22 constituting the wafer 1 are arrayed, will be parallel to the scanning direction of the X stage 31-1 and the scanning direction of the Y stage 31-2. Thus, the orientation of the wafer 1 placed on the placement table 34 is adjusted, and the slit-shaped beam 201 is irradiated to the wafer 1 having the orientation thereof adjusted.

The slit-shaped area 201-1 on the wafer 1 to which the slit-shaped beam 201 is irradiated is defined by adjusting the ray axis of the beam so that it will be perpendicular to the scanning direction X of the X stage 31-1 (the longitudinal direction of the slit-shaped beam 201 irradiated to the wafer 1 will be perpendicular to the scanning direction X of the X stage 31-1), parallel to the scanning direction Y of the Y stage 31-2 (the longitudinal direction of the slit-shaped beam 201 irradiated to the wafer 1 will be parallel to the scanning direction Y of the Y stage 31-2), and parallel to the direction in which the pixel locations in the photodetectors 26a and 26b are arrayed. This is advantageous in that when image signals representing the surfaces of chips are compared with each other, the chips can be readily aligned with each other. The slit-shaped beam 201 can be produced by inserting a conically curved lens 14, 224, or 234 shown in FIG. 3A, a cylindrical lens 255 shown in FIG. 3B, or a cylindrical lens 244 shown in FIG. 3C into a path.

For illuminations achieved in the directions 220 and 230 respectively shown in FIG. 2B, laser light shaped like a slit is irradiated to the slit-shaped area 201-1 on the wafer 1 in a direction that is laterally deviated by an angle φ from the Y-axis direction of the wafer and that meets the surface of the wafer 1 at an angle α (in FIG. 2B, a path along which illumination light propagating in the direction 230 is reflected from the mirror 233, passes through the cylindrical lens 234, and reaches the mirror 236 is shown superimposed on a path extending from the mirror 236 to the area 201-1 on the wafer 1 to which the slit-shaped beam 201 is irradiated).

Figure 3:
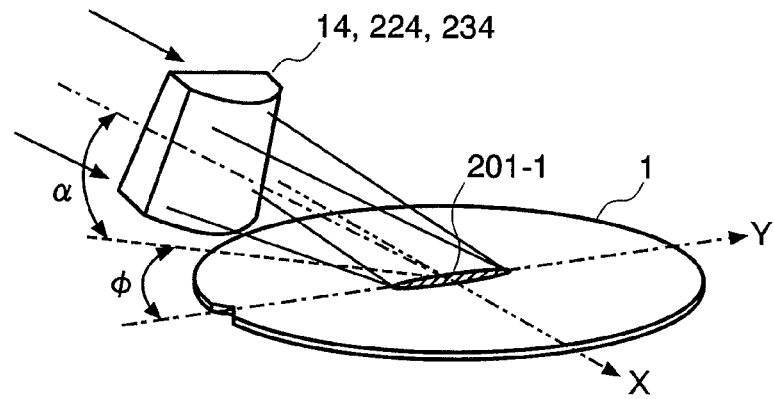
FIG. 3A is a perspective view showing a conically curved lens employed in an illuminative optical system that obliquely illuminates a linear area 201-1 on a wafer.
FIG. 3B is a perspective view showing a cylindrical lens employed in an illuminative optical system that longitudinally illuminates the linear area 201-1 on the wafer.
FIG. 3C is a perspective view showing a cylindrical lens employed in an illuminative optical system that laterally illuminates the linear area 201-1 on the wafer.
Figure 3:
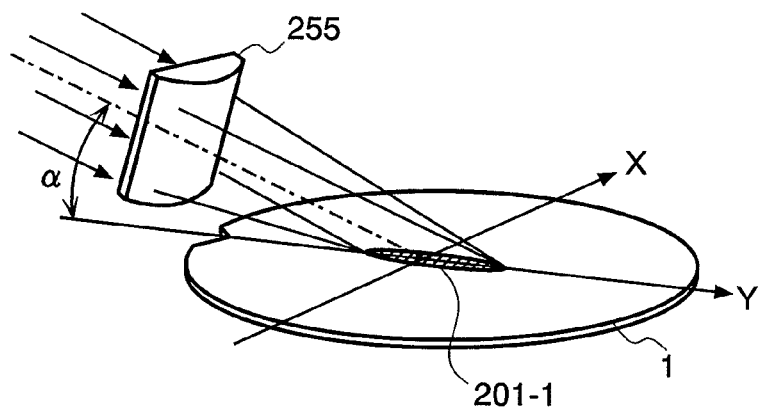
Figure 3:
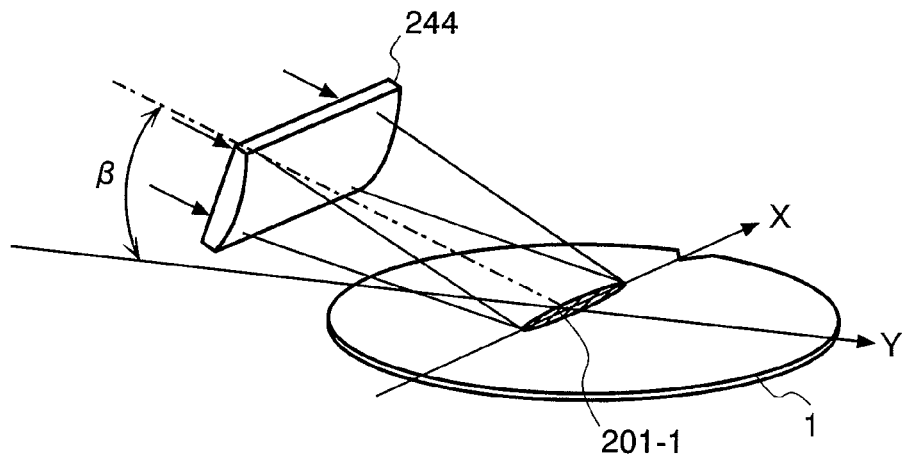

As an arrangement for realizing the foregoing illuminations, the conically curved lens 14 whose radius of curvature relative to the longitudinal direction varies continuously (corresponding to the lens 224 or 234 shown in FIG. 2B) is, as shown in FIG. 3A, disposed in the path so that the major-axis direction of the slit-shaped beam 201 that is irradiated to the wafer 1 will be parallel to the scanning direction of the Y stage 31-2 (the mirrors 225, 226, 235, and 236 are excluded from FIG. 3).

As for the illuminations achieved in the directions 240 and 250, since the illuminations are achieved in the same directions as the scanning directions of the X stage 31-1 and Y stage 31-2 respectively or the directions perpendicular to the scanning directions, the lens 255 shown in FIG. 3B (mirror 245 is excluded) or the lens 244 shown in FIG. 3C is used to produce the slit-shaped beam 201 so as to illuminate the slit-shaped area 201-1 on the wafer (in FIG. 3B and FIG. 3C, the lenses 244 and 255 are shown as cylindrical lenses but are not necessarily cylindrical when a shift of a position on which light irradiated to the wafer 1 is focused has to be compensated).

As shown in FIG. 2A, the mirror 15 (corresponding to the mirror 226 or 236 shown in FIG. 2B) and the mirror 205 (corresponding to the mirror 225 or 235 shown in FIG. 2B) are mechanically switched in response to a command issued from the overall control unit 50. Thus, an illuminating angle α can be varied depending on a kind of foreign matter to be detected on the substrate 1 to be inspected. As shown in FIG. 2C, whatever illuminating angle is designated, the slit-shaped area 201-1 on the wafer 1 to which the slit-shaped beam 201 is irradiated covers the direction 203 in which the pixel locations included in the photodetectors 26a and 26b are arrayed. In whatever directions including directions opposite to the directions 220 and 230 illumination is achieved, the position illuminated by the slit-shaped beam 201 corresponds to the slit-shaped area 201-1 on the wafer 1.

Consequently, illumination can be achieved at an angle φ of about 45° with light including rays parallel to the Y direction. In particular, when the slit-shaped beam 201 is composed of rays parallel to the Y direction, diffracted light emanating from circuit patterns whose major group of straight lines is oriented in the X and Y directions is intercepted by the spatial filter 22.

Incidentally, methods of manufacturing the conically curved lens 14 include a method described in, for example, Japanese Unexamined Patent Publication No. 2000-105203.

The reason why the slit-shaped beam 201 is irradiated to the slit-shaped area 201-1 on the wafer 1 at a plurality of illuminating angles is to detect various kinds of foreign matters present on the surface of the wafer 1. Specifically, a defective pattern on the substrate 1 to be inspected or a short foreign matter is detected.

A more microscopic foreign matter or defect must be detected in a portion of each of chips 202 constituting the wafer 1 in which the same pattern is repeatedly formed at intervals of a relatively narrow pitch in order to realize a memory unit or the like. A method conventionally known for detection of the microscopic foreign matter or defect is such that: relatively intense light is fed to the surface of the wafer 1 at a low angle with respect to the surface of the wafer; and diffracted light emanating from repetitive patterns formed closely at intervals of a relatively narrow pitch is intercepted by the spatial filter 22 in order to detect light reflected or scattered from the foreign matter or defect on the surface of the wafer 1. As a light source of the relatively intense light to be used to illuminate the surface of the wafer 1 at the low angle, a laser is suitable.

However, for detection of a foreign matter or defect in non-repetitive patterns formed to realize a logic unit or the like or loosely repetitive patterns formed at intervals of a relatively coarse pitch, since light scattered from the non-repetitive patterns or the loosely repetitive patterns formed at intervals of a relatively coarse pitch cannot be fully intercepted by the spatial filter, it is hard to extract only the light scattered from the foreign matter or defect from light reflected or scattered from the wafer 1. For detection of the foreign matter or defect in the non-repetitive patterns formed to realize a logic unit or the like, the wafer 1 should be illuminated in a direction of a relatively high angle. Thus, images of adjoining chips are detected and then compared with each other. However, when an attempt is made to detect a foreign matter or defect on the wafer 1 coated with an optically transparent film using a laser light source, since laser light falls within an extremely narrow range of wavelengths, if the thickness of the transparent film coated over the surface of the wafer varies to exhibit a distribution, the intensity of light reflected from the surface changes due to interference. This disables stable detection of a defect. According to the present embodiment, for detection of a foreign matter or defect in repetitive patterns, a light source whose light falls within a wide wavelength band is used to illuminate the wafer 1 in a direction of a relatively high angle in efforts to avoid the influence of the variation in the thickness of the transparent film coated over the surface of the wafer 1.

The present embodiment has an arrangement for realizing high-angle illumination that is achieved with light falling within a wide wavelength band and low-angle illumination that is achieved with single-wavelength light.

To begin with, a low-angle illumination optical system will be described in conjunction with FIG. 2A to FIG. 3C. FIG. 2A is an explanatory diagram concerning the principles of an arrangement that is the low-angle illumination optical system. With an increase in an illuminating angle α for low-angle illumination, an amount of light reflected and diffracted by circuit patterns increases, and a signal-to-noise ratio decreases. Therefore, an experimentally obtained optimal value is adopted. For example, for detection of a low foreign matter on the surface of a wafer, the illuminating angle α should be small, for example, should range from 1° to 10°, or preferably, from 1° to 5°.

As for an illuminating direction ϕ for low-angle illumination, for example, at a wiring step, the direction wiring patterns formed on a wafer and the illuminating direction are aligned with each other. This makes it easier to detect a foreign matter in wiring. Moreover, when circuit patterns on a wafer are not wiring patterns but consist of contact holes and capacitors, the circuit patterns have no particular directivity. Therefore, a chip containing the circuit patterns should be illuminated in a direction of about 45°. Talking of changing of illuminating angles, in the case of low-angle illumination, the two mirrors 15 and 205 whose angles are different from each other are, for example, as shown in FIG. 2A, switched. Otherwise, the angle of the mirror 15 (or 205) may be changed with the X direction (perpendicular to the sheet of paper of the drawing) as an axis of rotation using a rotating means that is not shown. At this time, the mirror 15 is moved even in the Z direction so that the ray axis of the slit-shaped beam 201 will be aligned on a wafer with the ray axis of light detected by the detective optical system. Moreover, the lens 14 is also moved in the Z direction so that the slit-shaped beam 201 will have a minimum diameter on the ray axis of the light detected by the detective optical system.

Next, a method for changing illuminating directions will be described in conjunction with FIG. 2B.

A branching optical element 218 shown in FIG. 2B is composed of a mirror, a prism, and others. A driving means that is not shown is used to move the branching optical element 218 in the Y direction, whereby laser light L0 emitted from the laser light source 11 is transmitted or reflected to propagate in any of three directions. Laser light L1 transmitted by the branching optical element 218 is branched into transmitted light and reflected light by a half prism 221. For example, after the transmitted light passes through a wave plate 236, it is reflected by a mirror 236 via a mirror 231, a beam diameter correction optical system 232, a mirror 233, and a conically curved lens 234. Consequently, the slit-shaped beam 201 enters the wafer 1 in the direction 230. Incidentally, the mirror 235 is disposed so that it can be inserted into or withdrawn from the space between the conically curved lens 234 and mirror 236, whereby an angle α of incidence at which the slit-shaped beam 201 formed by the conically curved lens 234 falls on the slit-shaped area 201-1 on the wafer can be changed from one to another.

On the other hand, light reflected from the half prism 221 is handled by an optical element having the same ability as the foregoing ability so that the slit-shaped beam 201 will be irradiated to the wafer 1 in the direction 220. Even in this path, a mirror 225 is disposed so that it can be inserted into or withdrawn from the space between a conically curved lens 224 and a mirror 226. Thus, an angle α of incidence at which the slit-shaped beam 201 formed by the conically curved lens 224 falls on the slit-shaped area 201-1 on the wafer can be changed from one to another. Incidentally, beam diameter correction optical systems 222 and 232 adjust the diameters of laser light waves incident on the conically curved lenses 234 and 224 respectively so that the slit-shaped beams 201 to be irradiated to the wafer 1 will have the same size. Moreover, if a mirror 260 is substituted for the half prism 221, illumination is achieved in the direction 220 alone. If neither the half prism 221 nor the mirror 260 is used, illumination is achieved in the direction 230 alone. Moreover, a wave plate 226 or 236 located behind the half prism 221 may be used to designate a direction of polarization of laser light to be irradiated so as to produce, for example, p-polarized light or s-polarized light alone.

After laser light L2 reflected from the branching optical element 218 passes through the beam diameter correction optical system 241, it is reflected from the mirrors 242 and 243, transmitted by a cylindrical lens 244 (see FIG. 3C), and reflected by a mirror 245. Consequently, a beam reshaped like a slit by the cylindrical lens 244 is irradiated to the slit-shaped area 201-1 on the wafer 1 in the direction 240.

On the other hand, laser light L3 is reflected by a mirror 251 in the same manner as light L2 is reflected by the foregoing optical element disposed on the path, and transmitted by a beam diameter correction optical system 252. Thereafter, the laser light is reflected from mirrors 253 and 254, transmitted by a cylindrical lens 255, and reflected by a mirror 256. Consequently, the slit-shaped beam 201 is irradiated to the wafer 1 in the direction 250.

As for the illuminating directions 240 and 250, if many wiring patterns formed on a wafer are parallel to the X or Y direction, the directions of illumination can be aligned with the X or Y direction at, for example, a wiring step. This is advantageous in that a foreign matter in wiring can be readily detected.

As the laser light source 11, a high-power YAG laser whose laser light contains a second harmonic having a wavelength of 532 nm is adopted. However, the wavelength need not always be 532 nm, and the fourth harmonic of the laser light having a wavelength of 266 nm may be utilized. Moreover, an ultraviolet, far-ultraviolet, or vacuum-ultraviolet laser, an Argon laser, a nitrogen laser, a He—Cd laser, an eximer laser, or a semiconductor layer may be adopted as a light source.

In general, when the wavelength of laser light is shortened, the resolution of a detected image improves. This permits high-sensitivity inspection.

Figure 4:
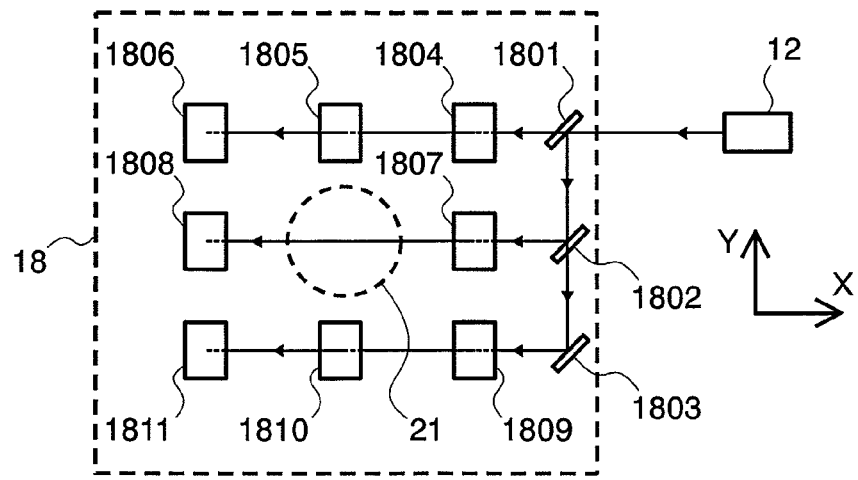
FIG. 4A is a plan view of a high-angle illumination optical system.
FIG. 4B is a front view of the high-angle illumination optical system.
FIG. 4C is an A-A sectional view of the high-angle illumination optical system.
Figure 4:
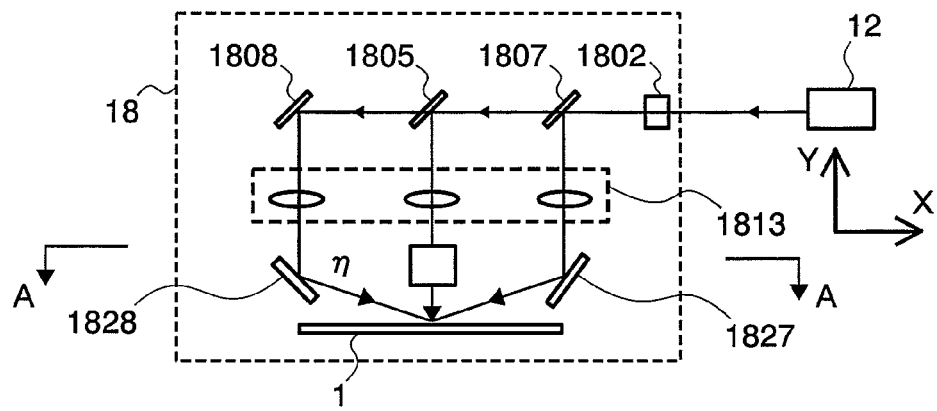
Figure 4:
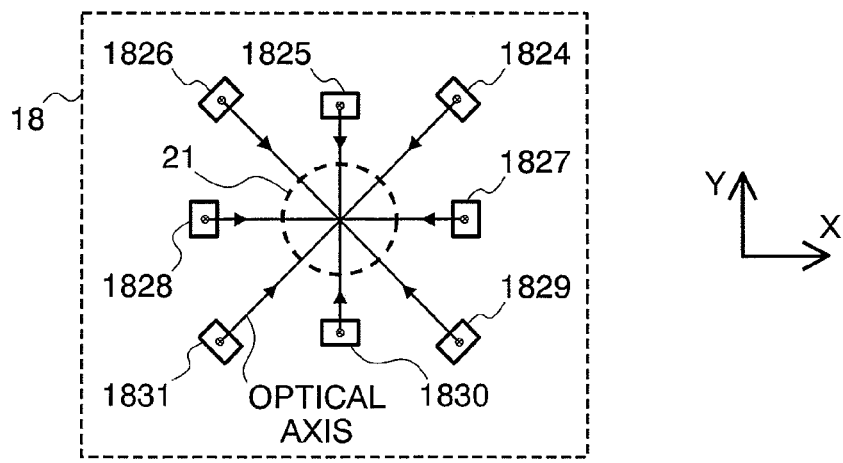

On the other hand, FIG. 4 shows in detail illumination to be achieved using a wide wavelength band, though the illumination light source 12 to be used for the illumination is illustrated in FIG. 1. In FIG. 4A to FIG. 4C, light falling within a wide wavelength band and emanating from the light source 12 is, as shown in FIG. 4A, branched into three paths by half-silvered mirrors 1801 and 1802 included in a high-angle illumination optical system 18. After the light waves have their paths angled by mirrors 1803 to 1811, the light waves are, as shown in FIG. 4B, converged on a group of condenser lenses 1813. Consequently, the substrate 1 to be inspected is illuminated in eight directions, which are equiangular directions with θ=45° between adjoining ones, by a group of mirrors 1824 to 1831. The transmittances of the mirrors 1801 to 1805, 1807, 1809, and 1810 disposed along the paths are determined so that the intensities of illuminations in the respective directions will be equal to one another on the substrate 1 to be inspected.

FIG. 5A and FIG. 5B show other examples of high-angle illumination. FIG. 5A shows an arrangement in which: a wavelength selection filter 2002 selects light, which falls within a specific range of wavelengths, from light that is emitted from a wide-band lamp light source 12 and that is transmitted by a lens 2001; after transmitted by a lens 2003, the selected light is routed to a half-silvered mirror 2005, which is interposed between the objective lens 21 and the spatial filter 22 or between the spatial filer 22 and the image formation lens 23, via collimator lenses 2004, and then irradiated using spherical mirrors 2006 so that the numerical aperture of the objective lens 21 will not be impaired. FIG. 5B shows an arrangement for irradiating light, which is emitted from the wide-band lamp light source 12, as it is without selecting a specific wavelength. For detection of a foreign matter in wiring at a wiring step or detection of a defective pattern, an illuminating angle η should be increased. However, in consideration of the relationship between a pattern and a signal-to-noise ratio for a signal acquired from a foreign matter, the illuminating angle η should range from 40° to 60°, or preferably, from 45° to 55°. Moreover, if a step of handling an object of inspection is associated with a kind of foreign matter to be detected, whatever illuminating angle is selected may be designated in an inspection plan.

Figure 5:
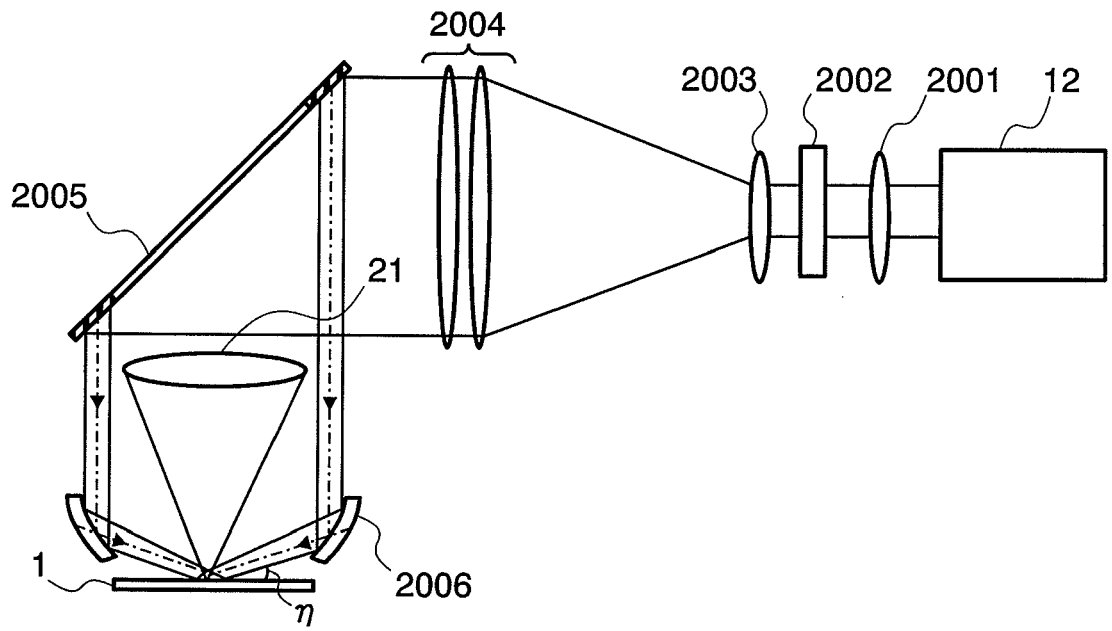
FIG. 5A is a schematic front view of a variant of the high-angle illumination optical system.
FIG. 5B is a schematic front view of another variant of the high-angle illumination optical system.
Figure 5:
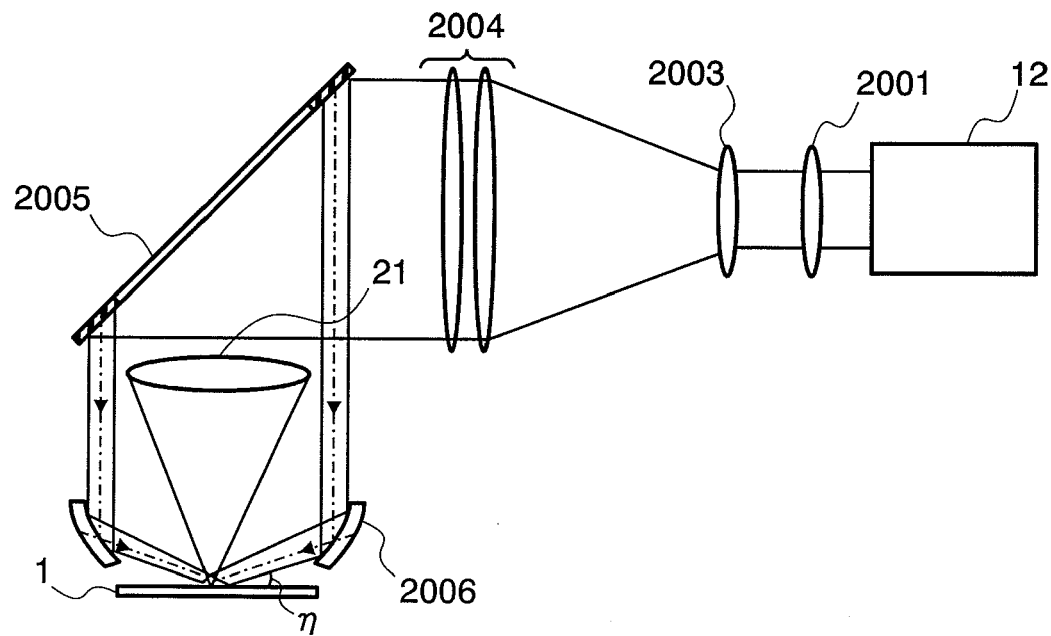

Moreover, for detection of all foreign matters or defective patterns on the surface of a wafer without leaving any foreign matter or defective pattern uninspected, the illuminating angle for high-angle illumination described in conjunction with FIG. 4 or FIG. 5 may be set to an intermediate range of the aforesaid range of values, that is, a range from 5° to 45°.

Figure 6:
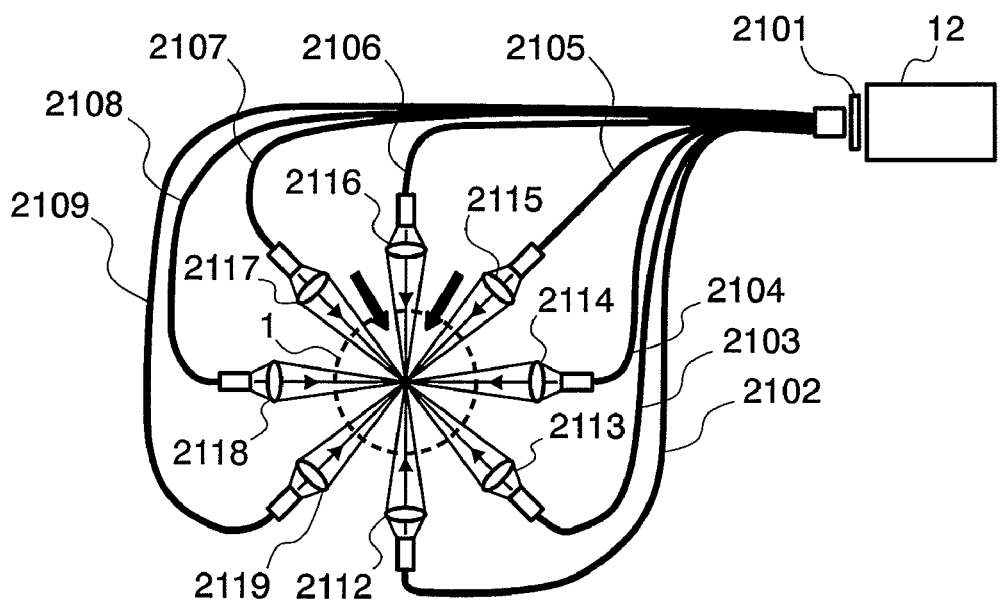
FIG. 6A is a schematic front view of still another variant of the high-angle illumination optical system.
FIG. 6B is a schematic front view of the variant shown in FIG. 6B.
Figure 6:
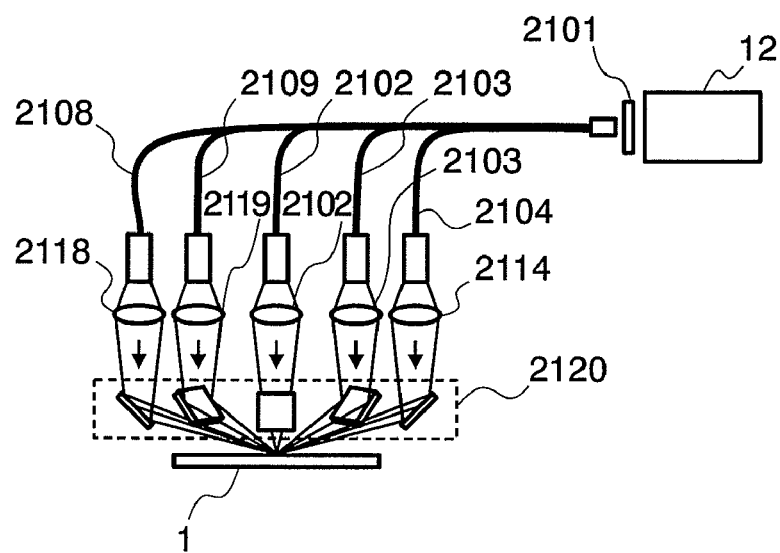

FIG. 6A and FIG. 6B show still other examples of high-angle illumination. As shown in FIG. 6A, light emitted from the light source 12 is propagated through a wavelength selection filter 2101, split into eight light waves by optical fibers 2102 to 2109, and converged on lenses 2112 to 2119 attached to the emission ends of the respective optical fibers. The light waves are then, as shown in FIG. 6B, reflected from a group of mirrors 2120 in order to change their paths. Consequently, high-angle illumination is performed on the wafer 1.

Next, the detective optical system 20 will be described below.

The detective optical system 20 is configured so that light reflected and diffracted by the substrate 1 to be inspected such as a wafer is detected by the photodetectors 26a and 26b, which are realized with TDI image sensors or the like, via the objective lens 21, spatial filter 22, image formation lens (variable-power image formation optical system) 23, optical filter 25 composed of a density filter and a sheet polarizer, and beam splitter 29. When the TDI sensors are adopted as the photodetectors 26a and 26b, the TDI sensors each having a plurality of output taps provide a plurality of signals concurrently. The signal processing system 40 manipulates the plurality of signals concurrently using a plurality of processing circuits or a plurality of pieces of processing software. Consequently, a defect can be detected quickly.

The spatial filter 22 has the ability to intercept a Fourier-transform image carried by light reflected and diffracted by repetitive patterns on the wafer 1 and pass light scattered from a defect or foreign matter. The spatial filter 22 is disposed in an area where it helps the objective lens 21 offer the spatial frequency, that is, at the position of an image plane on which a Fourier transform is formed (corresponding to an exit pupil). The spatial filter 22 exhibits an optical characteristic of intercepting a specific wavelength alone and transmitting the other wavelengths. Specifically, the spatial filter 22 intercepts light, which is diffracted by repetitive patterns formed in a memory unit or any other area and is derived from illumination light irradiated to the substrate 1 to be inspected, and passes light scattered from a defect or foreign matter. Moreover, the spatial filter 22 passes light diffracted by non-repetitive patterns on the surface of the substrate 1 to be inspected that is illuminated by the wide-band illumination light source 12. Light passing through the spatial filter 22 is separated into different wavelengths by the beam splitter 29. A wavelength identical to the wavelength of light emitted from the laser light source 11 is reflected to reach the photodetector 26a, and the other wavelengths are transmitted to reach the photodetector 26b. This makes it possible to avoid the saturation of each photodetector in terms of an amount of received light which is caused by light diffracted by the non-repetitive patterns.

Figure 8:
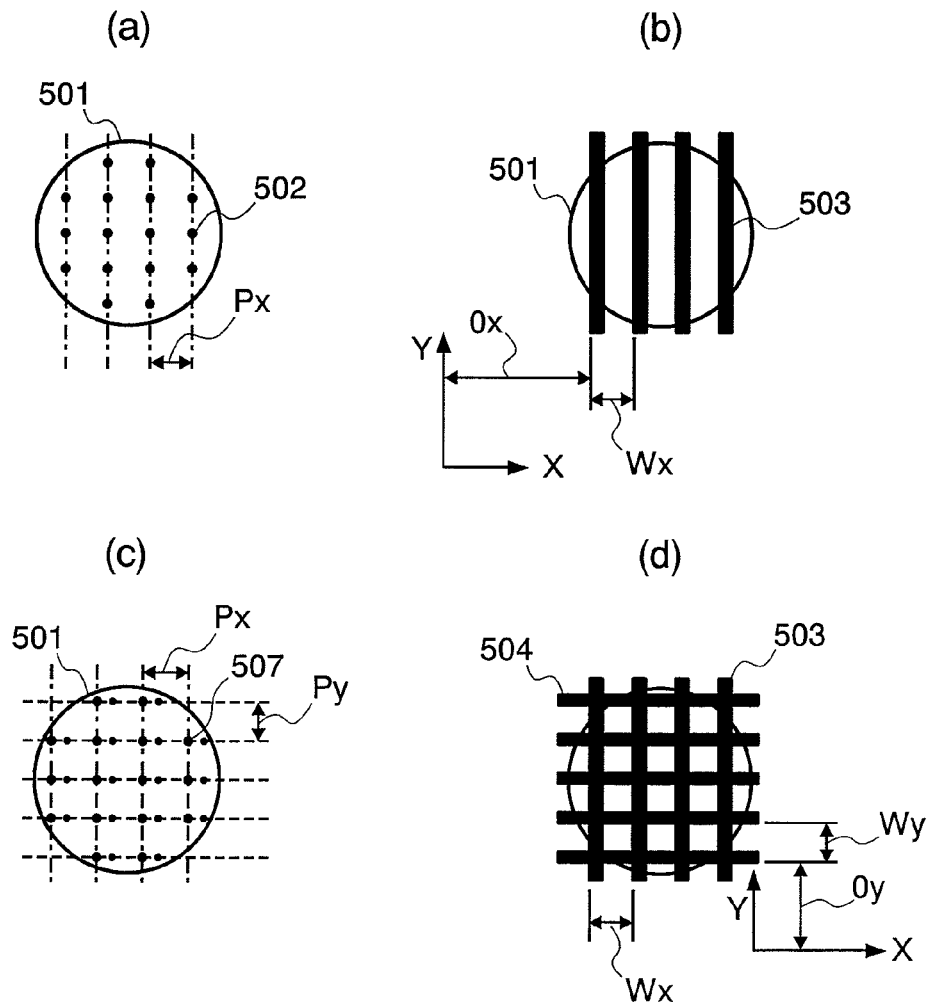
FIG. 8A shows a diffraction pattern produced by light reflected or scattered from a wafer when a pupil of an objective lens is viewed through a pupil viewing optical system.
FIG. 8B shows a state in which the diffraction pattern observed through the pupil viewing optical system is intercepted by a one-dimensional spatial filter.
FIG. 8C shows a diffraction pattern observed when the pupil of the objective lens is viewed through the pupil viewing optical system and the wafer is illuminated in multiple directions.
FIG. 8D shows a state in which a two-dimensional spatial filter is disposed in order to intercept the diffraction pattern shown in FIG. 8C.
Figure 9:
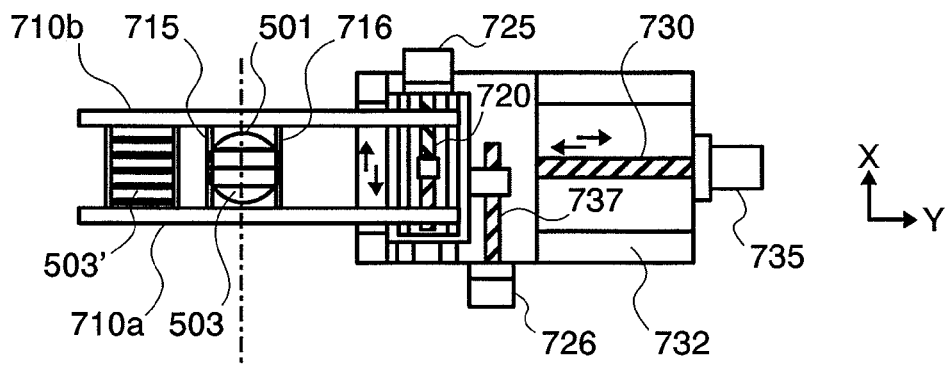
FIG. 9A is a plan view schematically showing the structure of a variable one-dimensional spatial filter.
FIG. 9B is a front view schematically showing the structure of the variable one-dimensional spatial filter.
FIG. 9C is a front view schematically showing the structure of a variable two-dimensional spatial filter.
FIG. 9D is a plan view showing a spring structure included in the variable two-dimensional spatial filter.
Figure 9:
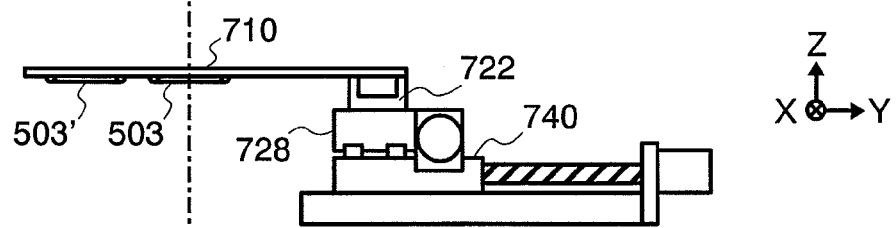
Figure 9:
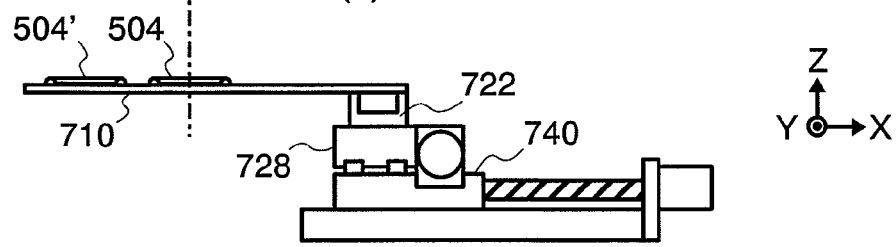
Figure 9:
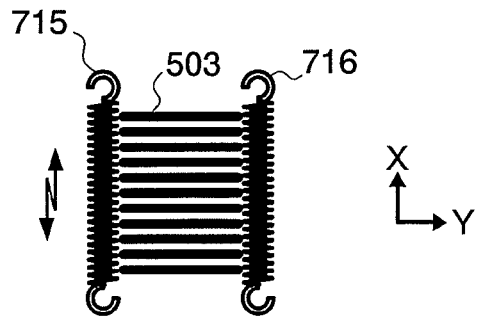

Incidentally, a pupil viewing optical system 70 that is composed of a mirror 90 which can withdraw in the Y direction during inspection, a projection lens 91, and a TV camera 92 and that is disposed along the optical axis of the detective optical system 20 is used to image bright points 502 (drawn with filled circles in FIG. 8A) in an image, which is carried by light reflected and diffracted by repetitive patterns and is viewed at the position of the image plane of a Fourier transform, within a field of view 501 offered by the pupil viewing optical system 70. A sheet interceptor 503 including a rectangular interceptor like the one shown in FIG. 8B is disposed at the position of the image plane of a Fourier transform. Both ends of the sheet interceptor 503 are, as shown in FIG. 9D, fixed to springs 715 and 716. The resultant sheet interceptor 503 is fixed to an arm 710 that includes, as shown in FIG. 9A and FIG. 9B, a motor 725, and a pair of members 710a and 710b capable of being opened or closed in the X direction by means of a feed screw 720 and a slide guide 722. A spacing Wx between adjoining ones of slats included in the sheet interceptor 503 is mechanically varied, and the entire sheet interceptor is moved along a guide 728 by means of a motor 726 and a feed screw 737 (in directions Ox in FIG. 8B). Thus, the rectangular interceptor is adjusted so that the spacing between adjoining slats will be equal to a pitch Px between adjoining ones of the bright points 502 in the reflected and diffracted light image. Specifically, the sheet interceptor 503 is, as shown in FIG. 8B, adjusted for fear the bright points in the image of the light reflected and diffracted by the repetitive patterns, which is viewed at the position of the image plane of a Fourier transform, may come out of the sheet interceptor 503.

As mentioned above, the spacing Wx between adjoining ones of the slats included in the sheet interceptor 503 is determined based on an actual image of patterns observed through the pupil viewing optical system 70. Moreover, design data representing patterns may be used to create a Fourier-transform image, and the spacing may be determined based on the image. Moreover, a sheet interceptor 503' whose interceptive width is different from that of the sheet interceptor 503 may be attached to the arm 710. In this case, if a table 740 bearing the entire arm 710 is moved in the Y direction along a guide 732 by means of a motor 735 and a feed screw 730 in order to switch the sheet interceptors, a change in the size of bright points in a reflected and diffracted light image can be coped with. The switching is performed in response to a command sent from the overall control unit 50 after a signal acquired by the TV camera 92 is manipulated by the signal processing system 95. Incidentally, the sheet interceptor 503 may not be employed. Alternatively, based on an image signal produced by the TV camera 92, an interceptor may be formed on a transparent substrate included in, for example, a liquid crystal display device, with black and white reversed, and substituted for the sheet interceptor 503.

FIG. 8C shows an image (bright points 507) that is carried by light reflected and diffracted by repetitive patterns and that is viewed at the position of the image plane of a Fourier transform within a field of view 501 offered by the pupil viewing optical system 70 when the wafer 1 is illuminated simultaneously in different directions. When the bright points 507 are laterally widened, a two-dimensional interceptive pattern that is, as shown in FIG. 8D, a combination of a lengthwise interceptive pattern 503 and a sideways interceptive pattern 504 is used to intercept the bright points 507 in the image carried by the light reflected and diffracted by the repetitive patterns formed on the wafer 1.

A sheet interceptor 504 having, as shown in FIG. 9C, the same structure as the one described in conjunction with FIG. 9A and FIG. 9B is included and superimposed on the sheet interceptor 503 so that the slats extending in the X and Y directions will intersect one another. In this case, the sheet interceptor 503 is placed on the bottom of the arm 710 including the pair of members that can be opened or closed, while the sheet interceptor 504 is placed on the top of the arm 710 so that it will jut out. Consequently, the interceptors will not be defocused in the Z direction on the plane containing the pupil of the objective lens 21.

Owing to the above arrangement, by adjusting the spacing Wx in the X direction between adjoining ones of the slats included in the sheet interceptor 503, the spacing Wy in the Y direction between adjoining ones of the slats included in the sheet interceptor 504, and the phases Ox and Oy of the sheet interceptor assembly, the spacings in the respective directions between adjoining ones of the slats included in the two-dimensional interceptive pattern made by combining the lengthwise interceptive pattern 503 and the sideways interceptive pattern 504 can be, as shown in FIG. 8D, adjusted.

Figure 10:
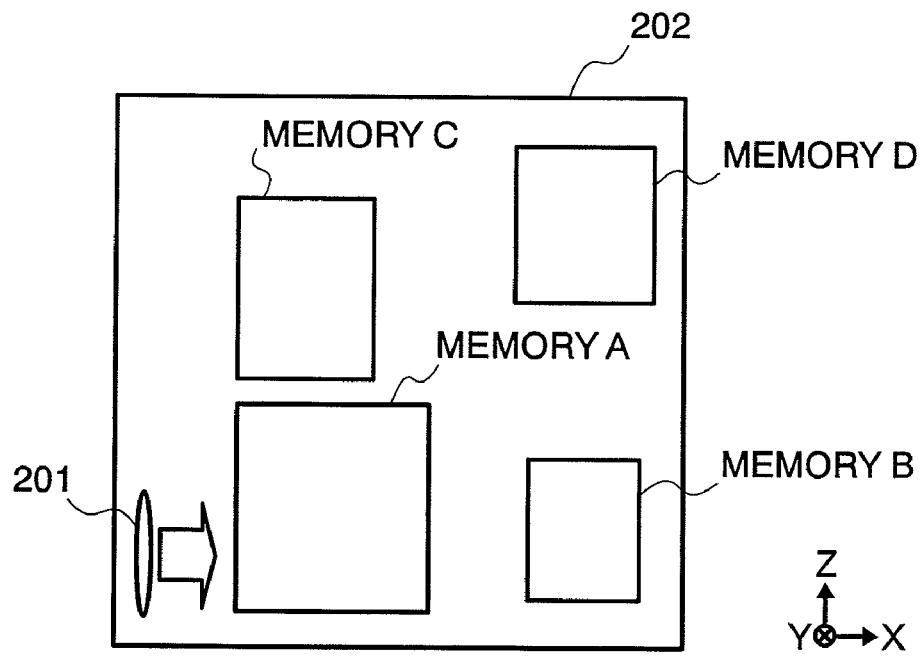
FIG. 10 is a plan view schematically showing the configuration of a chip of a semiconductor device formed on a wafer.

Consequently, as shown in FIG. 10, even when a plurality of memory units A to D exists in a chip, the spacings Wx and Wy between slats included in the interceptor included in the spatial filter are preserved during designation of conditions prior to inspection, and then designated immediately before the position of an area to be inspected is focused on. Thus, a microscopic defect can be detected highly sensitively.

In the present embodiment, the detective optical system 20 is designed to detect light, which is reflected or scattered from the wafer 1 after the wafer 1 is illuminated by irradiating laser light, which is emitted from the laser light source 11, via the low-angle illumination system as described in conjunction with FIG. 2A to FIG. 3C, separately from light that is reflected or scattered from the wafer 1 illuminated with light, which is emitted from the wide-band light source 12 and falls within a wide wavelength band, via the high-angle illumination system as described in conjunction with FIG. 4A to FIG. 6B. Specifically, the beam splitter 29 shown in FIG. 1 reflects light that is reflected or scattered from the wafer 1 illuminated with light irradiated via the low-angle illumination system. The photodetector 26a detects the reflected light. The beam splitter 29 transmits light that is reflected or scattered from the wafer 1 illuminated with light irradiated via the high-angle illumination system, and the photodetector 26b detects the transmitted light.

Figure 11:
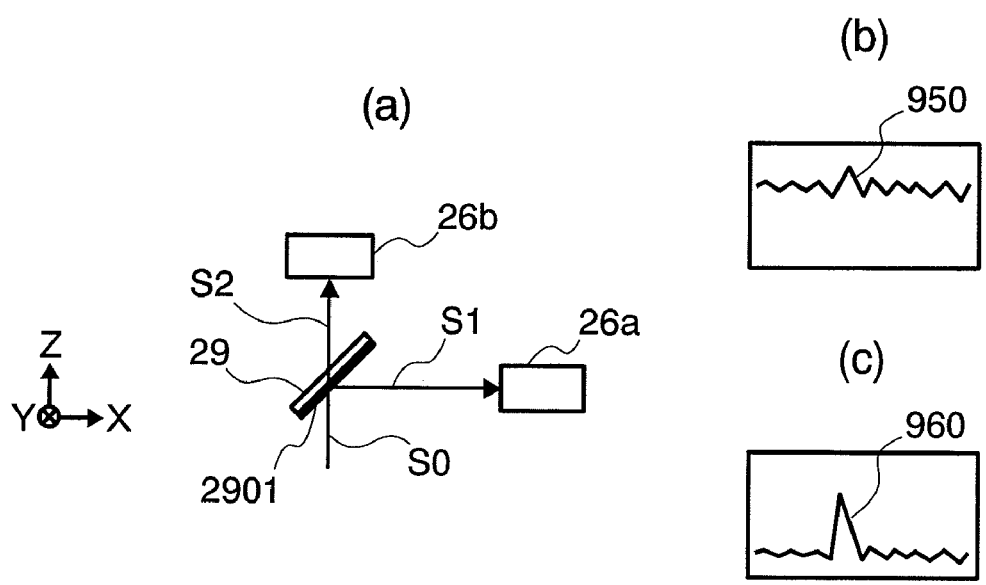
FIG. 11A is a front view for use in explaining in detail a detective optical system.
FIG. 11B shows a waveform of a detective signal produced when light S0 reflected or scattered from a wafer is detected.
FIG. 11C shows a waveform of a detective signal produced when light reflected or scattered under illumination with laser light is selected and detected.

FIG. 11A shows the detective optical system in detail. Herein, reference numeral S0 denotes light that is reflected or scattered from the wafer 1 and transmitted by the objective lens 21 and image formation lens 23. In the light, light reflected or scattered from the wafer 1 after irradiated via the low-angle illumination system, and light reflected or scattered from the wafer 1 after irradiated via the high-angle illumination system are mixed. The surface of the beam splitter 29 is coated with a thin film 2901 having a property of reflecting light whose wavelength is identical to that of laser light emitted from the laser light source 11. Among the components of the light S0 reflected or scattered from the wafer 1, a reflected or scattered light component S1 of laser light emitted from the laser light source 11 is reflected from the beam splitter 29 and then routed to the photodetector 26a. The detecting surface of the photodetector 26a (not shown) is located at the position of the image plane of an image formed by the image formation lens 23. The photodetector 26a detects an image of light reflected or scattered from the wafer 1 and derived from low-angle illumination achieved by the laser. On the other hand, the thin film 2901 coated over the surface of the beam splitter 29 transmits light having wavelengths other than the same wavelength as the wavelength of laser light. Therefore, a light component S2 reflected or scattered from the wafer 1 and derived from high-angle illumination achieved with light falling within a wide wavelength band enters the photodetector 26b located at the position of the image plane of an image formed by the image formation lens 23. The photodetector 26b detects a reflected or scattered light image derived from high-angle illumination achieved with light emitted from the wide-band light source 12.

Assuming that the light S0 reflected or scattered from the wafer 1 is not separated into the components S1 and S2 but detected as it is by the photodetector 26a, the detective signal has a defect signal 950 buried in noises as shown in FIG. 11B. On the other hand, when the component S1 is separated from the light S0 reflected or scattered from the wafer 1 and then detected by the photodetector 26a as it is in the present embodiment, the detective signal has a defect signal 960 distinguished as shown in FIG. 11C. Thus, the defect signal can be detected.

On the other hand, light emitted from the wide-band light source 12 for high-angle illumination is set to a lower intensity than light emitted from the laser light source 11 for low-angle illumination is. The photodetector 26b that detects light reflected or scattered from the wafer 1 and derived from low-angle illumination achieved by the wide-band light source 12 is set to a higher sensitivity than the photodetector 26a is. At this time, if the light component S1 were not separated from the light S0 reflected or scattered from the wafer 1 but were detected by the photodetector 26b, the photodetector 26b might be saturated due to the component S1. However, in the present embodiment, since the photodetector 26b detects the light S2 that remains intact with the component S1 separated from the light S0 reflected or scattered from the wafer 1, the photodetector will not be saturated but can stably detect light.

In the present embodiment, relatively high-luminance light reflected or scattered from a foreign matter on the surface of the wafer 1 and derived from low-angle illumination achieved with relatively high-luminance laser light emitted from the laser light source 11 is detected separately from light that is reflected or scattered from the surface of the wafer 1 and that is derived from high-angle illumination achieved with wide-band light emitted from the wide-band light source 12. Therefore, low-angle illumination with laser light and high-angle illumination with wide-band light can be achieved simultaneously. Consequently, the whole of the wafer 1 can be inspected during one inspection. Namely, both an area on the wafer 1 having repetitive patterns formed therein at intervals of a relatively small pitch (for example, patterns in a memory unit) and an area having patterns formed therein at intervals of a relatively large pitch (for example, non-memory patterns in a logic unit) can be continuously inspected to detect a defect without the necessity of switching optical systems.

The inspection system of the present embodiment supports both a mode in which foreign matter inspection is performed quickly and a mode in which high-sensitivity inspection is performed slowly. For an object of inspection or an area in which circuit patterns are formed at a high density, the power of the detective optical system is raised in order to acquire a high-resolution image signal. This permits highly sensitive inspection. Moreover, for an object of inspection or an area in which circuit patterns are formed at a low density, the power of the detective optical system is lowered in order to perform inspection quickly with high sensitivity maintained.

Consequently, the size of a foreign matter that should be detected and the size of a defect-detected pixel can be optimized. Noises caused by anything other than a foreign matter are removed, and only light scattered from the foreign matter can be detected efficiently. Namely, in the inspection system in accordance with the present embodiment, the power of the detective optical system 20 located above the wafer 1 can be varied using a simple arrangement.

Next, an arrangement for varying the power of the detective optical system and movements to be performed will be described in conjunction with FIG. 7.

The power of the detective optical system is varied in response to a command issued from the overall control unit 50. The image formation lens 23 includes movable lenses 401, 402, and 403 and a moving mechanism 404. When the power is varied, the magnification of a wafer surface image formed on the photodetector 26a or 26b can be varied without the necessity of changing the positions of the objective lens 21 and spatial filter 22 in an optical-axis direction. In other words, the relative positions between the substrate 1 to be inspected and the photodetector 26a or 26b need not be changed even at the time of varying the power. The moving mechanism 404 having a simple structure can be used to vary the power. Furthermore, since the size of the image plane of a Fourier transform remains unchanged, the spatial filter 22 need not be modified.

Assuming that $f_1$ denotes the focal length of the objective lens 21 and $f_2$ denotes the focal length of the image formation lens 23, the power M of the detective optical system 20 is calculated according to formula 1 presented below.

$$M=f_2/f_1 \quad (1)$$

In order to realize the power M of the variable-power detective optical system 20, since $f_1$ denotes a fixed value, the movable lenses are moved to positions permitting $f_2$ to assume the product of M by $f_1$.

Figure 7:
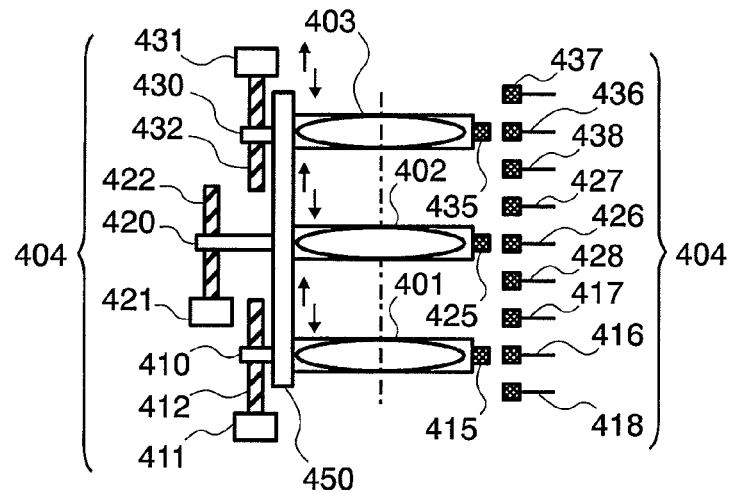
FIG. 7 is a front view schematically showing the elements of an objective lens.

FIG. 7 shows the configuration of the image formation lens 23 including the movable lenses 401 to 403 and the moving mechanism 404, and shows an arrangement for moving the movable lenses 401, 402, and 403 to specific positions so as to thus align them. The movable lens 401 is held by a lens holder 410, and the lens holder 410 moves in optical-axis directions along a linear guide 450 along with the rotation of a ball screw 412 driven by a motor 411. Likewise, the movable lenses 402 and 403 held by lens holders 420 and 430 respectively can move independently of each other in the optical-axis directions along the linear guide 450 along with the rotations of ball screws 422 and 432 respectively driven by motors 421 and 431 respectively.

Specifically, movable members 415, 425, and 435 included in alignment sensors are attached to the distal ends of the lens holders 410, 420, and 430 respectively that hold the movable lenses 401, 402, and 403 respectively. Detectors 416, 426, and 436 included in the alignment sensors are disposed at positions at which the movable lenses 401, 402, and 403 respectively are halted. The motors 411, 421, and 431 are driven in order to move the lens holders in the optical-axis directions. The alignment sensors 416, 426, and 436 disposed at positions permitting a desired power detect the movable members 415, 425, and 435 respectively so as to align them. Alignment sensors 417 and 418 serve as limit sensors for detecting the upper and lower limits in the optical-axis directions of a movable range of the movable lens 401. Likewise, limit sensors 427 and 428 and limit sensors 437 and 438 are included for the movable lenses 402 and 403 respectively. As the alignment sensor, an optical or magnetic sensor is conceivable.

The foregoing movements are performed in response to a command issued from the overall control unit 50. For example, when the circuit patterns formed on the substrate 1 to be inspected are highly dense, a high-power high-sensitivity inspection mode is designated. When the circuit patterns are less dense, quick inspection is performed with a low power. Thus, the power is appropriately designated so that many microscopic defects can be detected according to information on the surface of the substrate 1 to be inspected which is placed on the stages or according to a step included in a manufacturing process.

Next, a description will be made of a conditions-for-inspection designation sequence to be followed by the foreign matter or defect inspection system in accordance with the present invention.

Figure 12:
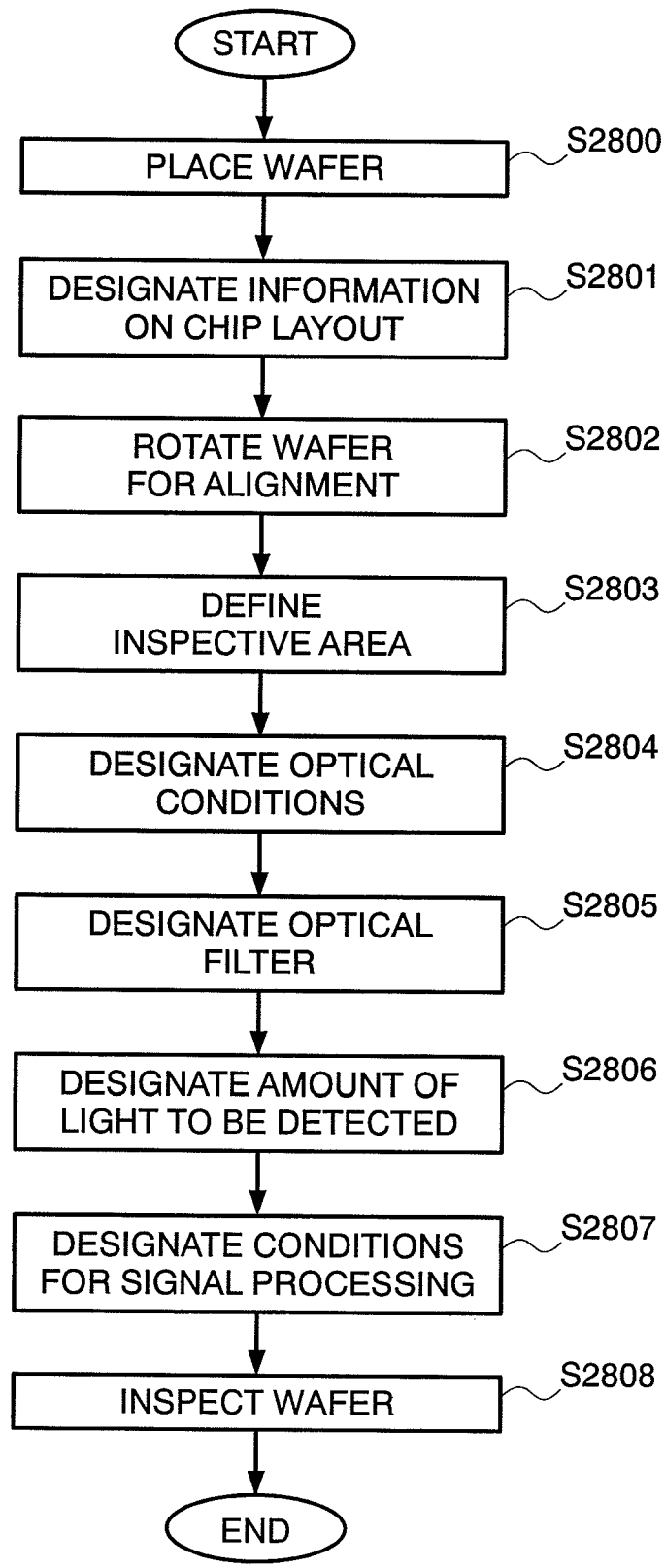
FIG. 12 is a flowchart describing an inspection procedure.

FIG. 12 is a flowchart describing designation of conditions for inspection. The wafer 1 is placed on the table 34 by a loader and immobilized by performing vacuum absorption (S2800). Chip layout information, that is, information on a chip size of a wafer or presence or absence of a chip in the wafer is designated (S2801). Thereafter, the entire wafer 1 is rotated so that the directions of arrays of chips 202 in the wafer 1 will run parallel to the edges of the photodetectors 26 (a rotation error is nearly nullified) (S2802). Thereafter, for inspection of each area on a wafer with optimal sensitivity, an inspective area is designated and detective sensitivity for the inspective area are designated (S2803). Thereafter, optical conditions such as a direction of illumination light to be irradiated to the wafer, an angle to be selected, and a power to be selected for the variable-power detective optical system 20 are designated (S2804). An optical filter is designated (S2805). An amount of light to be detected is designated (S2806). The conditions for signal processing are designated (S2807). Inspection is then initiated (S2808).

Figure 13:
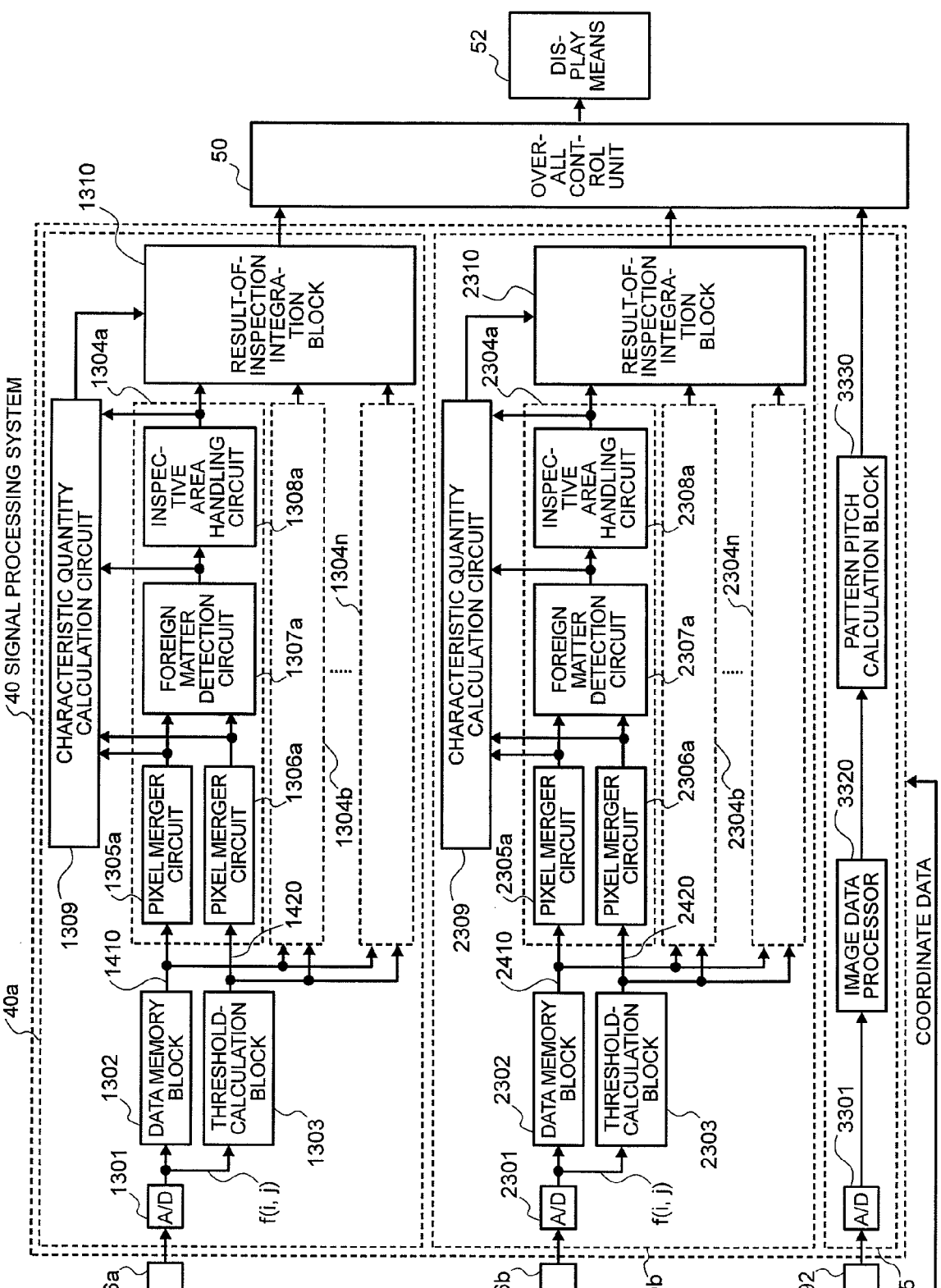
FIG. 13 is a block diagram showing in detail a signal processing system included in the first embodiment.

Next, manipulation to be performed on a detective signal at an inspection step (S2808) will be described below. Signals sent from the photodetectors 26 having received light reflected and diffracted by the surface of the wafer 1 are manipulated by the signal processing system 40. FIG. 13 shows the configuration of the signal processing system 40. Referring to FIG. 13, the signal processing system 40 includes processing circuits 40a, 40b, and 95 associated with the photodetectors 26a, 26b, and 92. When the number of detectors is increased, the number of processing circuits is increased accordingly.

The configuration of the processing circuit 40a and the actions to be performed thereby will be described below. The processing circuit 40a includes: an A/D converter 1301 that receives a detective signal from the detector 26a; a data memory block 1302 in which a detective image signal f(i,j) resulting from the A/D conversion is stored; a threshold calculation block 1303 that calculates a threshold on the basis of the detective image signal; foreign matter detection blocks 1304a to 1304n each of which includes as circuits, which detect a foreign matter at every merger of pixels on the basis of the detective image signal 1410 read from the data memory block 1302 and threshold image signals (Th(H), Th(Hm), Th(Lm), Th(L)) provided by the threshold calculation block 1303, pixel merger circuits 1305a and 1306a, a foreign matter detection circuit 1307a, and an inspective area handling circuit 1308a; a characteristic quantity calculation circuit 1309 that calculates a characteristic quantity such as an amount of scattered light obtained by detecting a defect under low-angle illumination, an amount of scattered light obtained by detecting a defect under high-angle illumination, or the number of detected pixels implying a degree of spread of a defect; and an integration block 1310 that classifies defects, which include small and large foreign matters on a semiconductor wafer, a defective pattern, and a micro-scratch, on the basis of the characteristic quantity calculated for each merger by the characteristic quantity calculation block 1309.

The foreign matter detection blocks 1304a to 1304n have the pixel merger circuits 1305a to 1305n and 1306 to 1306n, the foreign matter detection circuits 1307a to 1307n, and the inspective area handling circuits 1308a to 1308n respectively associated with respective merger operators that handle pixels the number of which corresponds to a product of, for example, 1×1, 3×3, 5×5, etc., or n×n.

A signal produced by the photodetector 26a is digitized by the A/D converter 1301. A detective image signal f(i,j) 1410 is stored in the data memory block 1302 and transferred to the threshold calculation block 1303. The threshold calculation block 1303 calculates a threshold image Th(i,j) 1420 to be used to detect a foreign matter. The foreign matter detection circuit 1307 detects a foreign matter on the basis of signals which the pixel merger circuits 1305 and 1306 have manipulated according to values produced by merger operators of an associated type.

The inspective area handling block 1308 manipulates a detected foreign matter signal and a threshold image in terms of a place of detection. Concurrently, based on signals produced by the pixel merger circuits 1305a to 1305n and 1306a to 1306n, the foreign matter detection circuits 1307a to 1307n, and the inspective area handling blocks 1308a to 1308n included in the respective foreign matter detection blocks 1304a to 1304n associated with the respective types of merger operators, the characteristic quantity calculation circuit 1309 calculates a characteristic quantity (for example, an amount of light scattered under high-angle illumination, an amount of light scattered under low-angle illumination, or the number of defect-detected pixels). The integration block 1310 integrates the foreign matter signal with the characteristic quantity, and transmits the resultant data to the overall control unit 50.

To be more specific, the A/D converter 1301 is a circuit having the ability to convert an analog signal produced by the photodetector 26 into a digital signal. The number of bits to be converted preferably ranges from 8 to 12 bits. If the number of bits is small, a resolution resulting from signal processing is low. This makes it hard to detect feeble light. On the other hand, if the number of bits is large, an expensive A/D converter is needed. This leads to the demerit that the price of the system gets high. The data memory block 1302 is a circuit in which the analog-to-digital converted signal is stored.

Figure 14:
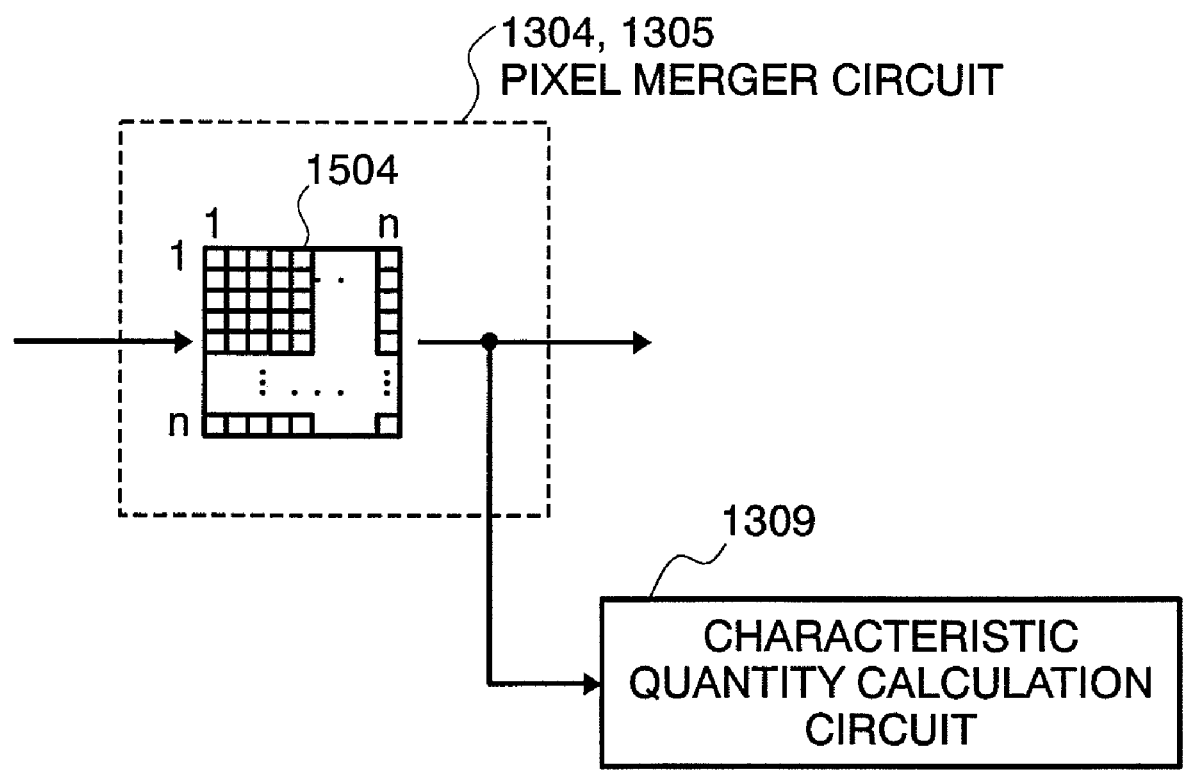
FIG. 14 is a block diagram showing in detail the configuration of a threshold calculation block included in the first embodiment.

Next, the pixel merger circuits 1305 and 1306 will be described in conjunction with FIG. 14.

The pixel merger circuits 1305a to 1305n and 1306a to 1306n include mutually different merger operators 1504.

The merger operators 1504 are facilities each of which merges detective image signals f(i,j) 1410 that are read from the data memory block 1302 and that represent respective pixels arrayed in n rows and n columns, and each of which merges difference threshold image signals 1420, each of which includes a detective threshold image signal Th(H), a detective threshold image signal Th(L), an inspective threshold image signal Th(Hm), and an inspective threshold image signal Th(Lm) that are produced by the threshold calculation block 1303, concerning the respective pixels arrayed in n rows and n columns. The merger operators 1504 are, for example, circuits each of which produces mean values relevant to the pixels arrayed in n rows and n columns.

The pixel merger circuits 1305a and 1306a include merger operators each of which merges a value relevant to, for example, a pixel arrayed in one row and one column. The pixel merger circuits 1305b and 1306b include merger operators each of which merges values relevant to pixels arrayed in three rows and three columns. The pixel merger circuits 1305c and 1306c include merger operators each of which merges values relevant to pixels arrayed in five rows and five columns. The pixel merger circuits 1305n and 1306n include merger operators each of which merges values relevant to pixels arrayed in n rows and n columns. The merger operators that merge a value relevant to a pixel arrayed in one row and one column provide input signals 1410 and 1420 respectively as they are.

The threshold image signal includes, as mentioned above, four image signals (Th(H), Th(Hm), Th(Lm), and Th(L)). Therefore, each of the pixel merger circuits 1306a to 1306n needs four merger operators Op. Consequently, the pixel merger circuits 1305a to 1305n transmit merged detective image signals 431a to 431n that are the results of merger of detective image signals performed by the merger operators 1504. On the other hand, the pixel merger circuits 1306a to 1306n transmit merged threshold image signals 441a (441a1 to 441a4) to 441n (441n1 to 441n4) that are the results of merger of four sets of threshold image signals (Th(H), Th(Hm), Th(Lm), Th(L)) performed by the merger operators Op1 to Opn. The merger operators included in the respective pixel merger circuits 1306a to 1306n are identical to one another.

The advantage of merger of values relevant to pixels will be described below. Foreign matter inspection should detect not only a microscopic foreign matter but also a large thin-film-like foreign matter that spreads over a range of several micrometers wide. However, a detective image signal acquired from the thin-film-like foreign matter is not always intense enough. Therefore, a detective image signal representing a pixel exhibits a low signal-to-noise ratio and may therefore be left unfound. Therefore, every set of pixels arrayed in n rows and n columns of which size corresponds to the size of the thin-film foreign matter is cut out and convoluted to other set of pixels, whereby the signal-to-noise ratio is improved.

Next, the inspective area handling blocks 1308a to 1308n will be described below.

The inspective area handling blocks 1308a to 1308n are employed in a case where data representing an area (including an area within a chip) that need not be inspected is removed from a foreign matter or defect detective signal acquired from a specific chip by each of the foreign matter detection circuits 1307a to 1307n, in a case where a detective sensitivity has to be changed area by area (including an area within a chip), or in a case where an area to be inspected is selected.

Regarding the inspective area handling blocks 1308a to 1308n, for example, when the detective sensitivity for an area on the substrate 1 to be inspected may be low, a threshold for the area calculated by a threshold calculator 1411 included in the threshold calculation block 1303 may be set to a large value. Otherwise, data representing a foreign matter in an area that should be inspected may be extracted from data items representing foreign matters, which are produced by each of the foreign matter detection circuits 1307a to 1307n, on the basis of coordinates representing the position of the foreign matter.

An area for which detective sensitivity may be low is, for example, an area on the substrate 1 to be inspected where the density of circuit patterns is low. The merit of lowering the detective sensitivity is that the number of foreign matters to be detected is efficiently decreased. A high-sensitivity inspection system may detect as many as several ten thousands of foreign matters. At this time, what is most significant is a foreign matter in an area in which circuit patters exist. Taking measures against the significant foreign matter provides a shortcut to improvement in a yield of device manufacture.

However, when the whole of the substrate 1 to be inspected is inspected with the same sensitivity, since a significant foreign matter and an insignificant foreign matter coexist, the significant foreign matter cannot be readily extracted. Therefore, the inspective area handling blocks 1308a to 1308n are used to lower the detective sensitivity for an area, of which foreign matter do not adversely affect a yield and in which no circuit pattern exists, on the basis of CAD information on each chip or threshold map information. Thus, the significant foreign matter can be efficiently extracted. However, a method of extracting a foreign matter is not limited to the method of changing detective sensitivity. Alternatively, foreign matters may be classified as described later in order to extract a significant foreign matter or the significant foreign matter may be extracted based on the sizes of foreign matters.

Next, the characteristic quantity calculation circuit 1309 will be described below.

What is referred to as a characteristic quantity is a value representing the characteristic of a detected foreign matter or defect. The characteristic quantity calculation circuit 1309 is a processing circuit for calculating the characteristic quantity. The characteristic quantity is, for example, an amount of light reflected and diffracted by a foreign matter or defect and derived from high-angle illumination or low-angle illumination (an amount of scattered light) (Dh,Dl), the number of defect-detected pixels, the shape of a foreign matter-detected area, the direction of a principal axis of inertia, a place on a wafer where a foreign matter is detected, a type of circuit patterns on a substrate, or a threshold for detection of a foreign matter.

Next, the integration block 1310 will be described below.

The integration block 1310 has the ability to integrate the results of foreign matter detections concurrently performed by the pixel merger circuits 1305 and 1306 respectively or integrate a characteristic quantity calculated by the characteristic quantity calculation circuit 1309 with the results of foreign matter detection (positional information on a foreign matter or defect) and to transmit the result of the integration to the overall control unit 50. The integration of the results of inspection should preferably be performed by a personal computer or the like so that the contents of processing can be easily modified.

The processing circuit 40b performs the same processing as the foregoing processing circuit 40a does. An image signal produced by the photodetector 26b that has detected light reflected or scattered under high-angle illumination is manipulated by the components ranging from an A/D converter 2301 to a results-of-inspection integration block 2310 in order to detect a foreign matter or defect. The characteristic quantity concerning the foreign matter or defect is then calculated.

The overall control unit 50 adds up (ORs) foreign matter or defect detective signals, which have been manipulated by the results-of-inspection integration blocks 1310 and 2310 so as to specify the position and characteristic quantity of a foreign matter or defect existing on the wafer 1. Information on the specified foreign matter or defect is displayed on the screen of the display means 52 in the form of a map representing the surface of a wafer or a histogram one of whose axes indicate sizes.

On the other hand, an image signal representing bright points in an image that is carried by light reflected and diffracted by repetitive patterns formed on the wafer 1 and that is picked up by the TV camera 92 and viewed at the position of the image plane of a Fourier transform in the detective optical system 20 is transferred to the signal processing circuit 95, converted into a digital signal by an A/D converter 3301, and then manipulated as image data by an image data processor 3320. The signal manipulated as image data by the image data processor 3320 is transferred to a pattern pitch arithmetic block 3330. A pitch Px between adjoining ones of bright points 502 in a reflected and diffracted light image is calculated. Data representing the pitch Px of the bright points 502 and the image data are transferred to the overall control unit 50, and then transmitted as a signal, with which the pitches Wx and Wy between adjoining ones of slats included in the interceptive patterns 503 and 504 incorporated in the spatial filter 22 are controlled, to a spatial filter control unit 27.

In the present embodiment, while both low-angle illumination based on laser light and high-angle illumination based on wide-band light are performed concurrently, the wafer 1 is inspected for foreign matters or defects. An image carried by light that is a component of light reflected or scattered from the surface of the wafer 1 as a result of the low-angle illumination based on laser light and that is not intercepted by the spatial filter 22 but reflected from the beam splitter 29 is detected by the photodetector 26a and transferred to a processing circuit. A diffraction pattern produced by light that is a component of light reflected or scattered from the surface of the wafer 1 after light falls on the wafer at a low angle and that is scattered from repetitive patterns formed on the wafer 1 at intervals of a relatively small pitch is intercepted by the spatial filter and then detected. Moreover, multi-wavelength light emitted from the lamp light source is caused to fall on the surface of the wafer 1 at a relatively high angle. Light reflected or scattered from the surface of the wafer 1 is detected separately from light scattered under illumination based on single-wavelength laser light. Consequently, during one inspection, both an area on the wafer 1 having repetitive patterns formed therein at intervals of a relatively small pitch (for example, patterns in a memory unit) and an area having patterns formed therein at intervals of a relatively large pitch (for example, non-memory patterns in a logic unit or the like) can be inspected in order to detect defects.

Second Embodiment

During foreign matter inspection, even a multilayer wafer having a transparent film (for example, an oxide film) coated over the surface thereof must be inspected. The multilayer wafer is manufactured by repeating a step of forming patterns on the transparent film. There is an increasing need for detection of only foreign matters on the surface of an oxide film during inspection of a wafer having the oxide films formed therein. Fundamentally, by decreasing an illuminating angle α, an adverse effect of pattern-diffracted light or light reflected from a substrate can be suppressed. However, the decrease in the illuminating angle α poses a problem in that: light that is a regularly reflected component of illumination light, that is, forward scattered light occupies a majority of light scattered from a foreign matter; an amount of scattered light incident on a detective optical system located above gets smaller; and the foreign matter cannot therefore be detected stably.

Figure 15:
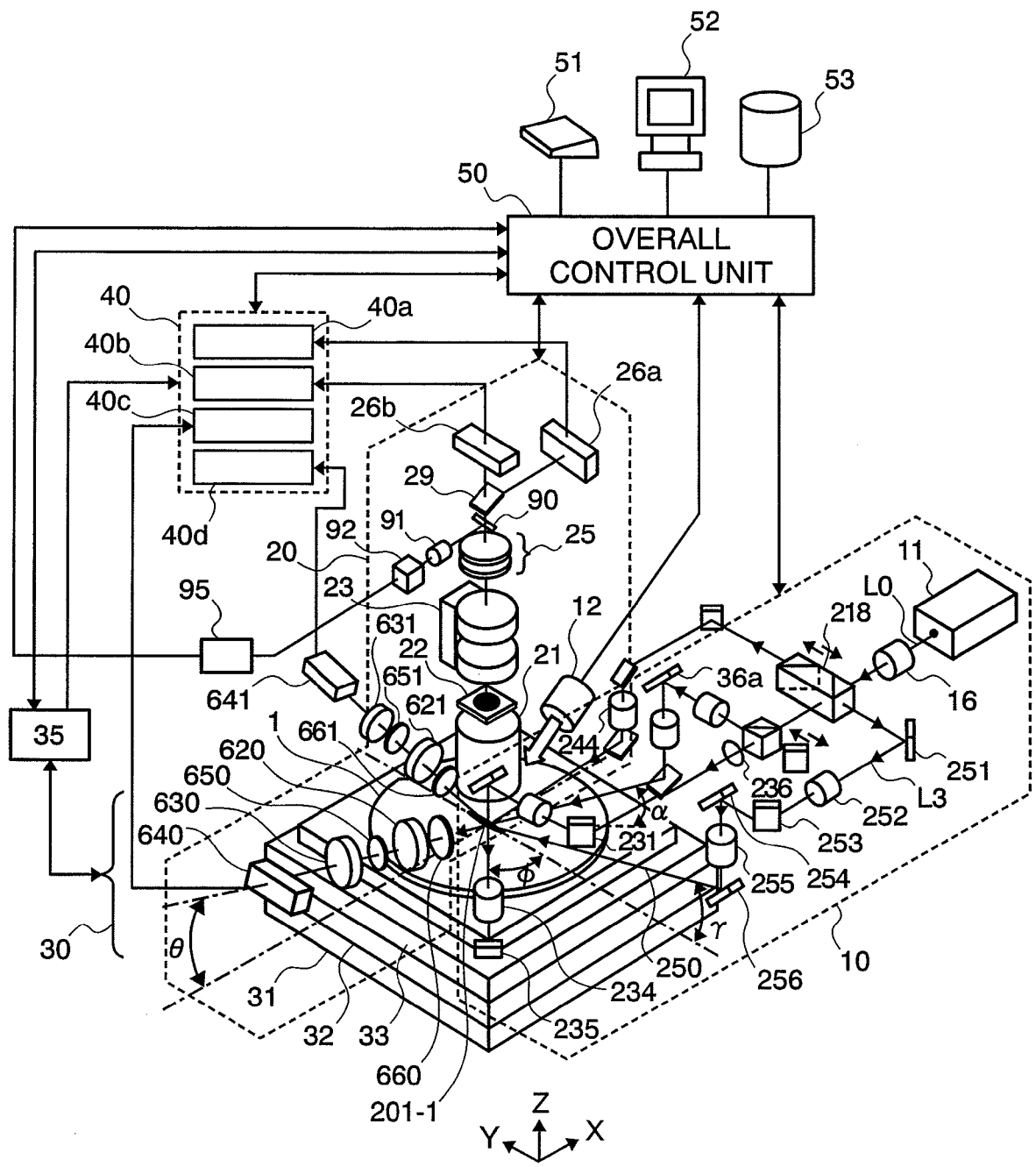
FIG. 15 is a perspective view showing the overall configuration of a defect inspection system in accordance with the second embodiment.

In the second embodiment, a system shown in FIG. 15 is used to detect light, which is reflected or scattered from the wafer 1 as a result of illumination, not only from above the wafer but also from obliquely above it. In FIG. 15, an illuminative optical system 10 has basically the same elements as the one shown in FIG. 2B and includes a low-angle illumination optical system that includes a laser light source 11 and a high-angle illumination optical system that includes a wide-band light source 12. Parts assigned the same reference numerals as those shown in FIG. 2B and parts located at the same positions of parts shown in FIG. 2B but assigned no reference numeral have the same abilities as those described in conjunction with FIG. 2B.

In the configuration shown in FIG. 15, laser light emitted from the laser light source 11, having the diameter thereof enlarged by a beam enlargement optical system 16, and reflected in the direction of a path L3 by a branching optical element 218 passes through a mirror 251, a beam diameter correction optical system 252, mirrors 253 and 254, a cylindrical lens 255, and a mirror 256. The light is then irradiated to an area 201-1 on the surface of a wafer 1 in an illuminating direction 250 at an illuminating angle γ in the form of a slit-shaped beam 201. A detective optical system composed of an optical filter 660, an objective lens 620, a spatial filter 650, an image formation lens 630, and a detector 640 is disposed in a direction 260 that intersects the illuminating direction 250 and that meets a Y-axis direction at a horizontal angle Φ ((not shown) and meets the surface of the wafer 1 at a detecting angle θ. The slit-shaped beam 201 is irradiated to the wafer in the illuminating direction 250, whereby light laterally scattered from a foreign matter present on the surface of a thin film coated over the wafer is detected. The light receiving surface of the detector 640 and an area on the surface of the wafer to which the slit-shaped beam 201 is irradiated have a relationship of image formation. The power of the image formation lens 630 is determined so that the light receiving surface of the detector will cover an entire range illuminated with the slit-shaped beam 201.

On the other hand, light scattered upward from a foreign matter existent on the surface of a thin film coated over a wafer illuminated with the slit-shaped beam 201 in the illuminating direction 250 is converged on an objective lens 21. Moreover, out of light reflected or scattered from the wafer 1 due to wide-band illumination light waves emitted from illumination light emission ends 121a and 121b of optical fibers 2102 to 2109 shown in FIG. 6 by which light that falls within a wide wavelength band and is emitted from an illuminative optical system 12 is branched into a plurality of paths, upward scattered light is converged on the objective lens 21. As described in relation to the first embodiment, the scattered light waves have the wavelengths thereof separated from each other and are then detected by photodetectors 26a and 26b respectively.

A detective system is designed to form an image. This has the merits that stray light other than light reflected or scattered from an object of detection is prevented from giving an adverse effect and that inspection is speeded up because parallel processing can be performed. An automatic focusing control system that is not shown controls a detector so that the light receiving surface 203 of the detector will be disposed in a range illuminated with the slit-shaped beam 201. Thus, the surface of the wafer is, without fail, located at a certain position in the Z direction during inspection.

As shown in FIG. 15, the present embodiment includes, in addition to a detective optical system whose elements range from the objective lens 21 to the photodetectors 26a and 26b and which is disposed perpendicularly to the surface of the wafer 1, a first oblique detection system whose elements range from a wavelength selection filter 660 to a photodetector 640, and a second oblique detection system whose elements range from a wavelength selection filter 661 to a photodetector 641. The detector 640 included in the first oblique detection system and the detector 641 included in the second oblique detection system are, similarly to the detectors 26a and 26b, realized with TDI image sensors respectively. Moreover, a spatial filter 650 or 651 having the same ability as the spatial filter 22 described in conjunction with FIG. 1 is disposed along the optical axis of the oblique detection system in order to intercept light reflected and diffracted by patterns. Furthermore, a thin film that selectively transmits light which has the same wavelength as laser light emitted from a laser light source 11 is coated over the surfaces of the wavelength selection filters 660 and 661 respectively. Thus, a component of light reflected or scattered from the wafer 1 owing to high-angle illumination achieved by a wide-wavelength band light source 12 is cut and detected. Lenses 620 and 621 are objective lenses, and lenses 630 and 631 are image formation lenses.

The position of the second oblique detection system is not limited to the one shown in FIG. 15 but the second oblique detection system may be opposed to the first oblique detection system. When the second oblique detection system is opposed to the first oblique detection system, if the wafer 1 is illuminated obliquely in the illuminating direction 250, the results of detections performed by the first and second detection systems respectively are combined in order to obtain a large number of pieces of information on reflected or scattered light waves.

As for the illuminating direction, illumination may be performed in a direction 220 or a direction 230. However, an illuminating means and a detective optical system composed of the image formation lens 630 and detector 640 should preferably be disposed for fear they may be interfere with each other, and directed or angled in order to avoid an adverse effect of light reflected from the substrate such as light diffracted by patterns. Namely, the illuminating means and detective optical system should preferably be located at experimentally determined optimal positions.

Image signals detected by the detector 640 included in the first oblique detection system and the detector 641 included in the second oblique detection system respectively are manipulated by signal processing systems 40c and 40d respectively. The manipulation of the detected image signals is identical to that described in conjunction with FIG. 13. An iterative description will be omitted.

Third Embodiment

Figure 16:
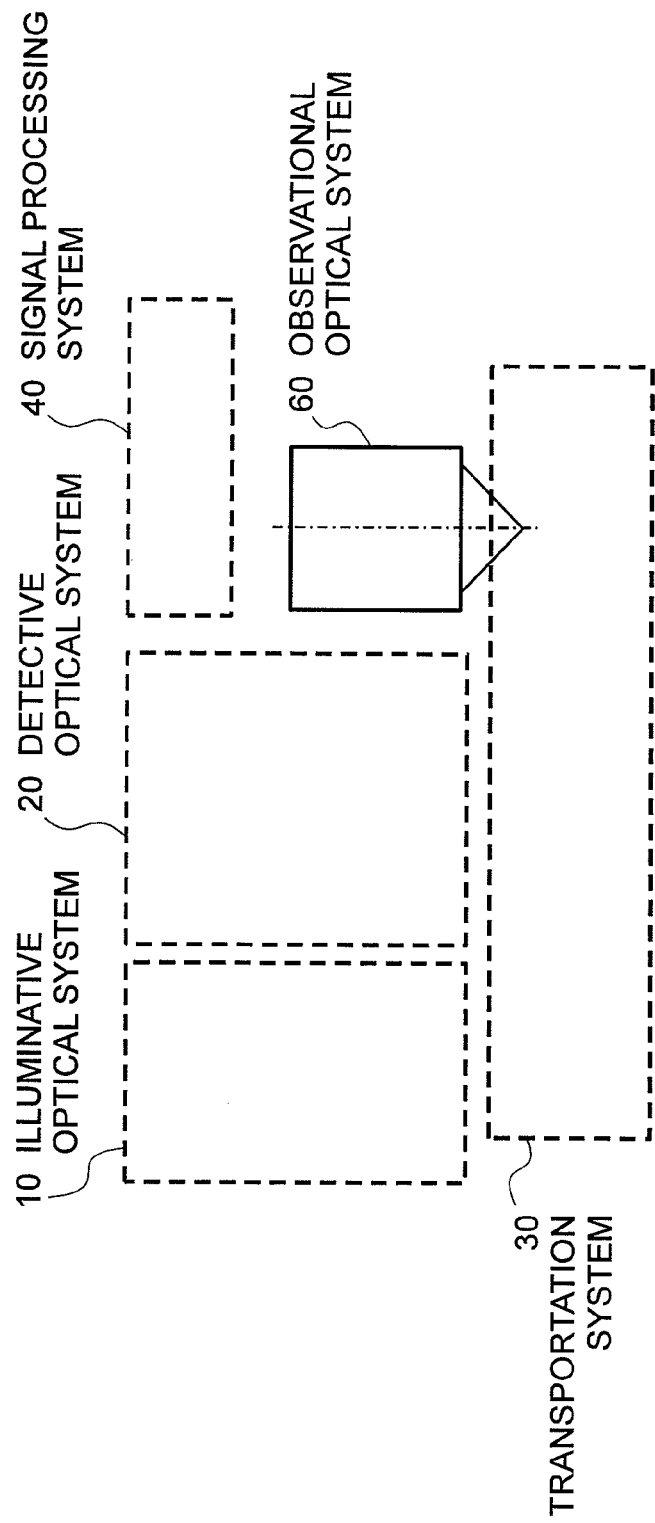
FIG. 16 schematically shows a defect inspection system in accordance with the third embodiment including an observational optical system.

FIG. 16 shows an embodiment of a defect inspection system including a microscope. In the present embodiment, a foreign matter detected during inspection can be verified using an observational optical system 60.

A detected foreign matter (including a quasi foreign matter) on the wafer 1 is moved to a position within a field of view offered by a microscope included in the observational optical system 60 by moving stages 31 and 32. The foreign matter is then observed.

The advantage provided by the inclusion of the observational optical system 60 lies in a point that a detected foreign matter can be immediately observed without the necessity of moving a wafer to a reviewer such as a scanning electron microscope (SEM). Since a foreign matter detected by an inspection system can be immediately observed, a cause of occurrence of the foreign matter can be identified quickly. Moreover, an image of a detected foreign matter picked up by a TV camera 64 included in the observational optical system 60 is displayed on a color monitor that is shared by a personal computer. Also included is a facility capable of irradiating laser light to part of a wafer centered on a detected foreign matter, scanning the wafer by moving stages for inspection, marking a scattered light image of the foreign matter and the position of the foreign matter, and displaying the marked image and position on a monitor. Consequently, whether a foreign matter is actually detected can be verified. As an image of part of a wafer scanned by moving the stages, an image of a die adjoining a die in which a foreign matter is detected may be picked up. Comparison and verification can be achieved immediately.

As a microscope included in the observational optical system 60, either a microscope employing a light source that emits visible light (for example, white light) or a microscope employing a light source that emits ultraviolet light may be adopted. For observation of an especially microscopic foreign matter, a high-resolution microscope, for example, the microscope based on ultraviolet light is preferred. The adoption of the microscope based on visible light provides color information on a foreign matter. This is advantageous in that the foreign matter can be readily recognized.

Fourth Embodiment

Figure 17:
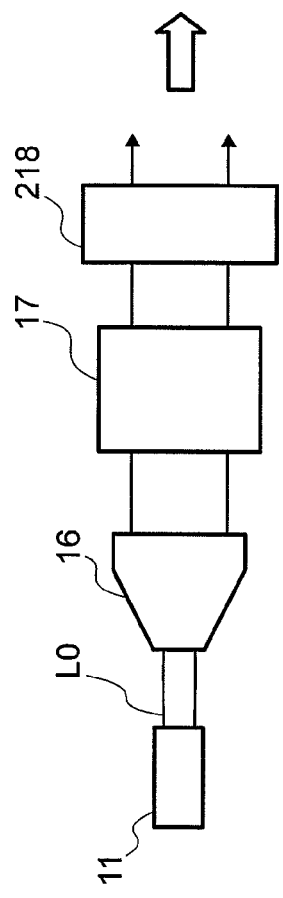
FIG. 17 is a plan view showing the arrangement of elements of a path branching optical system included in the fourth embodiment.
Figure 18:
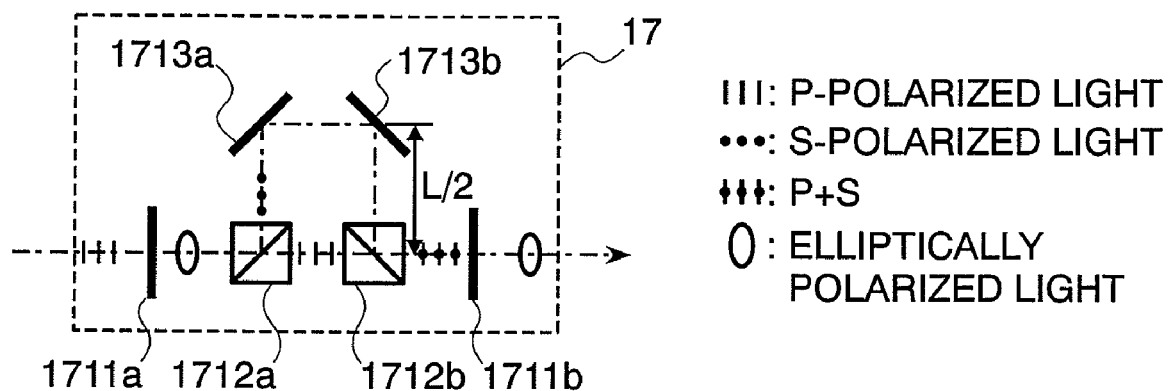
FIG. 18A is a block diagram schematically showing the path branching optical system included in the fourth embodiment.
FIG. 18B shows a waveform of a signal of pulsed laser light emitted from a laser light source.
FIG. 18C shows a waveform of pulses demonstrating that one pulse of laser light emitted from the laser light source is split into two pulses.
Figure 18:
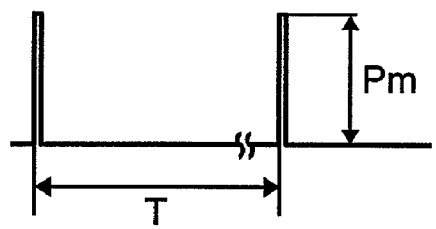
Figure 18:
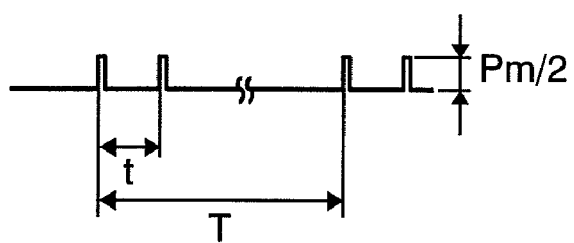
Figure 19:
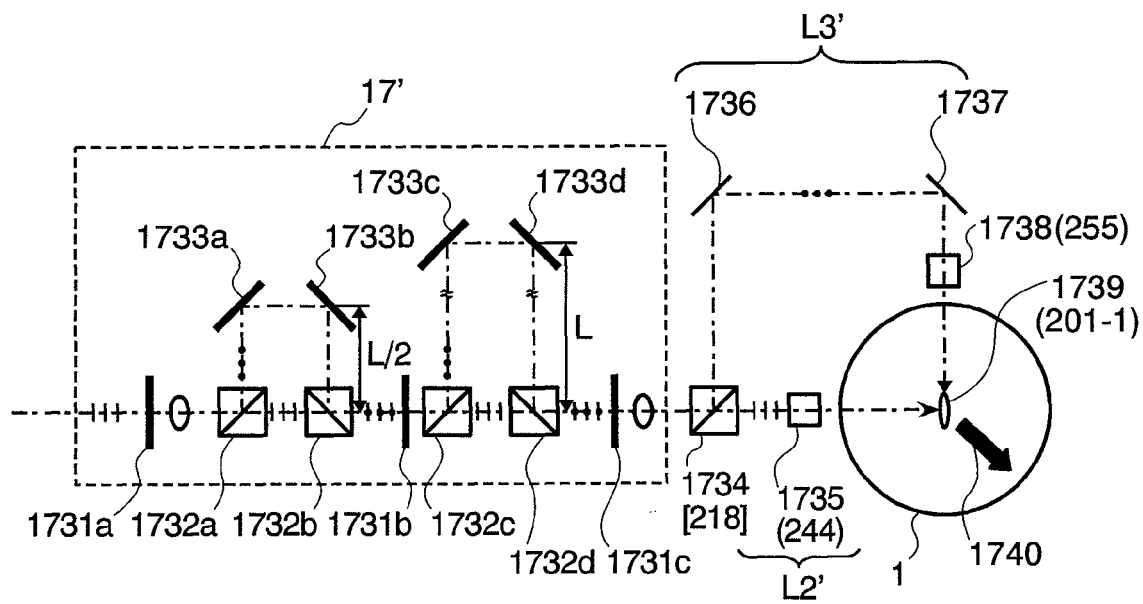
FIG. 19A is a block diagram schematically showing the elements of a path branching optical system included in a variant of the fourth embodiment.
FIG. 19B shows a waveform of pulses demonstrating split of a pulse.
Figure 19:
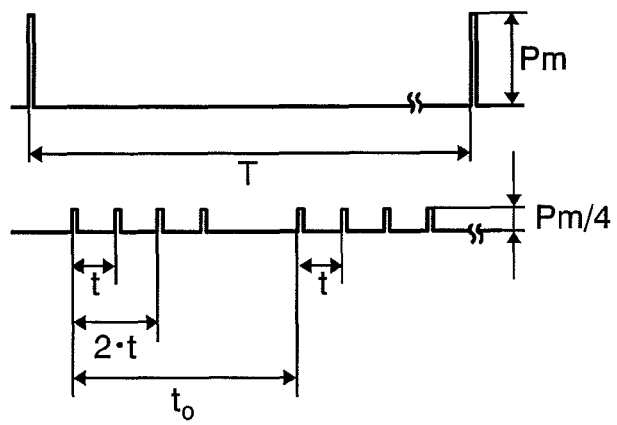

Referring to FIG. 17 to FIG. 19, a description will be made of another embodiment that adopts as the low-angle illumination light source 11 an ultraviolet laser such as a KrF laser or an ArF laser and that includes the low-angle illumination optical system 10 included the arrangement shown in FIG. 2B or FIG. 15.

An amount of light scattered from a microscopic particle of 0.1 μm or less in diameter is inversely proportional to the fourth power of the wavelength of illumination light. Therefore, the employment of light having a short wavelength permits higher sensitivity. In order to improve the sensitivity in detecting a defect, an ultraviolet laser emitting light of a shorter wavelength is adopted as an illumination light source. Moreover, for detection of light reflected or scattered from a microscopic foreign matter or defect, an amount of illumination light should be large.

When a pulsed oscillation laser is adopted as the ultraviolet laser, a peak value (maximum power) of power provided by the pulsed oscillation laser is much larger than a required mean power. For example, assuming that the mean power of a laser is 2 W, the emission frequency of light emitted therefrom is 100 MHz, the pulse spacing thereof is 10 ns, and the pulse width thereof is 10 ps, the peak value (maximum power) is so large as 2 kW that it may damage a specimen. Consequently, the peak value (maximum power) should preferably be decreased with the mean power held intact.

As for a method of decreasing the peak value with the mean power sustained, as shown in FIG. 17, a laser beam L0 emitted from the light source 11 is enlarged by a beam enlargement optical system 16, and routed to a pulse branching optical system 17 so that the laser beam will be branched into a plurality of paths whose path lengths are different from one another. Thereafter, the light paths are integrated into one. Thus, one pulse of laser light emitted from the light source is divided into a plurality of pulses having a smaller peak value. The plurality of pulsed laser light waves is routed to a branching optical element 218 so that the light waves will be introduced to any of the directions of paths L1, L2, or L3 shown in FIG. 2B or FIG. 15. Thus, the light waves are recomposed into a slit-shaped beam which is then irradiated to a slit-shaped area 201-1 on the wafer 1.

Since a pulsed laser beam is split into a plurality of components and then irradiated, assuming that the moving speed of an X stage 31-1 on which a substrate W to be inspected is placed is 20 cm per sec and the size of a field of view offered by one pixel location in a photodetector 26a or 26b is 1 μm, when an ultraviolet pulsed laser beam whose frequency is 100 MHz is split into a plurality of components under the aforesaid conditions, several hundreds or more of pulses of laser light are repeatedly irradiated to an area to be detected by one pixel location in the detector 26a or 26b. Consequently, speckle noises derived from a laser beam can be temporally averaged for imaging. This results in an image having noises minimized.

FIG. 18A shows an example of a pulsed light split optical system 17. In this example, the pulsed light split optical system 17 includes quarter-wave plates 1711a and 1711b, polarization beam splitters (PBS) 1712a and 1712b, and mirrors 1713a and 1713b. The quarter-wave plate 1711a transforms an incident laser beam, which is enlarged by the beam enlargement optical system 16 and is linearly polarized (p-polarized light in this example), into elliptically polarized light. The polarization beam splitter 1712a separates the elliptically polarized light into p-polarized light and s-polarized light. One of the polarized light waves, that is, the p-polarized light passes through the polarization beam splitter 1712a and polarization beam splitter 1712b. The other s-polarized light is reflected from the polarization beam splitter 1712a, mirrors 1713a and 1713b, and polarization beam splitter 1712b, and returned to the same optical axis as the p-polarized light having passed through the polarization beam splitters 1712a and 1712b is. At this time, assuming that the spacing between the polarization beam splitter 1712a and mirror 1713a or between the polarization beam splitter 1712b and mirror 1713b is L/2 m, the path of the s-polarized light and the path of the p-polarized light have an optical path difference of L m. Assuming that the light velocity is c m/s, the s-polarized light and p-polarized light have a temporal difference expressed by formula 2 below.

$$t(s)=L(m)/c(m/s) \quad (2)$$

A beam containing two pulses that have a time interval T between them as shown in FIG. 18B and being emitted from the laser light source 11 is temporally split. Consequently, as shown in FIG. 18C, one pulse is split into two pulses having a time interval t between them in order to halve the peak value of the pulse.

For example, assume that laser light having a pulse spacing of 10 nm ($10^{-8}$ sec) and a pulse width of 10 ps ($10^{-11}$ sec) is employed and the spacing between the polarization beam splitter 1712a and mirror 1713a or between the polarization beam splitter 1712b and mirror 1713b is set to 15 cm (0.15 m). In this case, the temporal difference between the s-polarized light and p-polarized light is 1 ns ($10^{-9}$ sec). Consequently, a pulsed laser beam whose peak value is halved is irradiated to the surface of a wafer twice at intervals of 1 ns within 10 ns.

The angle of rotation of the quarter-wave plate 1711a is adjusted so that the ratio of s-polarized light to p-polarized light in a beam incident on the polarization beam splitter 1712a will be 1:1 (circularly polarized light). Due to a loss in reflectance or transmittance caused by employed optical elements (polarization beam splitters 1712a and 1712b and mirrors 1713a and 1713b), the peak values of s-polarized pulsed light and p-polarized pulsed light separated from a beam emitted from the polarization beam splitter 1712b become different from each other. In order to decrease a maximum value to be assumed by the peaks of respective pulsed light waves, the peak values of the respective pulsed light waves must be equal to each other.

According to the configuration of the pulse split optical system 17 shown in FIG. 18A, p-polarized light is affected by the transmittance (Tp) of p-polarized light offered by the polarization beam splitters 1712a and 1712b. In contrast, s-polarized light is affected by both the reflectance (Rs) of s-polarized light offered by the polarization beam splitters 1712a and 1712b and the reflectance (Rm) of s-polarized light offered by the mirrors 1713a and 1713b. Assuming that Ls denotes a loss of s-polarized light and Lp denotes a loss of p-polarized light, a loss ratio (Pl) is expressed by formula 3 below.

$$Pl=Ls/Lp=Rm^2 \times Rs^2/Tp^2 \quad (3)$$

Consequently, when the angle of rotation of the quarter-wave plate 1711a is adjusted so that the ellipticity of polarized light incident on the polarization beam splitter 1712a will be equal to the loss ratio, the peak values of s-polarized pulsed light and p-polarized pulsed light into which light emitted from the polarization beam splitter 1712b is separated become nearly equal to each other. The p-polarized pulsed light and s-polarized pulsed light that are separated to have the nearly equal peak value are transmitted by the quarter-wave plate 1711b to become circularly polarized light waves.

The method of halving pulsed light using the pulse split optical system 17 has been described. Referring to FIG. 19A and FIG. 19B, a method of quartering pulsed light will be described in relation to a variant of the pulse split optical system 17 that splits pulsed light into a larger number of components. The configuration of a pulse split optical system 17' shown in FIG. 19A includes two stages of the pulse split optical system 17 shown in FIG. 18A. The spacing between a polarization beam splitter 1732c and a mirror 1733c or between a polarization beam splitter 1732d and a mirror 1733d included in the second stage is set to a double of the spacing between a polarization beam splitter 1732a and a mirror 1733a or between a polarization beam splitter 1732b and a mirror 1733b included in the first stage. Light emitted from the polarization beam splitter 1732b in the first stage includes p-polarized pulsed light and s-polarized pulsed light that lags behind the p-polarized pulsed light. The optical pulse train is recomposed into circularly polarized light by a quarter-wave plate 1731b. P-polarized light whose intensity is a half of the intensity of the optical pulse train transmitted by the quarter-wave plate 1731b is transmitted by the polarization beam splitters 1732c and 1732d. S-polarized light whose intensity is a half of the intensity of the pulse train is reflected from the polarization beam splitter 1732c and mirrors 1733c and 1733d, reflected from the polarization beam splitter 1732d, and returned to the same optical axis as the p-polarized light is. Consequently, pulsed light is quartered, and the peak values of the quarters are a quarter of the peak value of the pulsed laser beam emitted from the light source 11. Strictly speaking, since optical elements causes loses in reflectance or transmittance as mentioned above, the peak value is smaller than the quarter.

In the configuration shown in FIG. 19A, p-polarized pulsed laser light having passed through the polarization beam splitters 1732c and 1732d and s-polarized pulsed laser light reflected from the mirror 1733d and polarization beam splitter 1732d propagate along the same optical axis, are recomposed into circularly polarized light by the quarter-wave plate 1731c, and then falls on the polarization beam splitter 1734 (equivalent to the branching optical element 218 shown FIG. 2B or FIG. 15). Consequently, the circularly polarized light is separated into p-polarized light and s-polarized light. One of the polarized light waves, that is, the p-polarized laser light is propagated along a path L2' equivalent to the path L2 shown in FIG. 2B or FIG. 15, and then reshaped by a cylindrical lens 1735 (equivalent to the cylindrical lens 244 in the path L2 shown in FIG. 2B or FIG. 15). The resultant light illuminates a linear area 1793 on the wafer 1 (equivalent to the linear area 201-1 on the wafer 1 shown in FIG. 2B or FIG. 15).

On the other hand, the s-polarized light reflected from the polarization beam splitter 1734 and thus angled 90° is propagated along a path L3' equivalent to the path L3 shown in FIG. 2B or FIG. 15, reflected from mirrors 1736 and 1737 to have the path changed to another, and then reshaped by a cylindrical lens 1738 (equivalent to the cylindrical lens 255 in the path L3 shown in FIG. 2B or FIG. 15). The resultant light illuminates, unlike p-polarized laser light that illuminates the wafer in the direction of the path L2', the linear area 1793 on the wafer 1 perpendicularly to the wafer 1.

The path L2' and path L3' are designed so that the optical lengths thereof will be different from each other. As shown in FIG. 19B, p-polarized laser light and s-polarized light that are irradiated to the linear area 1793 on the wafer 1 are irradiated at different timings that have a temporal difference to proportional to an optical path difference. Consequently, interference between the p-polarized laser light and s-polarized laser light that are irradiated to the linear area 1793 can be prevented.

Moreover, the photodetector 26a that detects light reflected or scattered under illumination with the laser light source 11 detects light reflected or scattered under illumination performed in a direction deviated by 90° within a period of time during which the photodetector detects one pixel. Consequently, a variance in detective sensitivity attributable to a difference in an illuminating direction can be minimized. Eventually, a more microscopic foreign matter or defect can be stably detected. At this time, a direction of detection is the direction of an arrow 1740. Moreover, as for the photodetector, either or both of the detectors 640 and 641 described in conjunction with FIG. 15 may be employed.

According to the present embodiment, an ultraviolet pulsed laser beam can be irradiated to a wafer with the peak value thereof decreased. A quite microscopic defect having a diameter of about 0.1 µm or less can be detected without any damage to the wafer.

According to the present invention, an object of inspection is illuminated with single-wavelength light and wide-wavelength band light, which are different from each other in a wavelength band, in efforts to stably detect a defect on the surface of the object of inspection. A spatial filter having the ability to intercept light diffracted by repetitive patterns and pass light diffracted by non-repetitive patterns is disposed at a position in a detective optical system at which a Fourier transform is observed. A means is included for designating conditions for the spatial filter on the basis of an image of light diffracted by actual patterns which is viewed at the position of a Fourier transform, or an image of light diffracted from patterns which is supposed to be viewed on the image plane of a Fourier transform and is produced based on design data representing patterns formed on the surface of the object of inspection. Light scattered from the surface of a specimen and transmitted by the spatial filter is separated into light components of different wavelengths. An image is detected by a detector and compared with an image of an adjoining die within the same specimen in order to detect a microscopic defect. Thus, light diffracted by circuit patterns on a substrate such as LSI patterns is reduced so that a microscopic foreign matter or defect, a foreign matter or defect causing a short circuit of wiring, or a thin-film-like foreign matter can be detected quickly and highly precisely.

Moreover, according to the present invention, one pulse of laser light emitted from a pulsed laser light source designed for low-angle illumination is split into a plurality of pulses in order to decrease the peak value. The resultant laser light is irradiated to a specimen. Consequently, a high-luminance pulsed laser may be used to detect a more microscopic foreign matter. Nevertheless, the more microscopic foreign matter can be stably detected without any damage to the specimen.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An apparatus for inspecting a specimen comprising:
a first illumination unit having a laser source which emits a laser and a first optical component which illuminates a specimen on which patterns are formed with the laser from a first elevation angle;
a second illumination unit having a light source which emits a light having plural wavelengths and a second optical component which illuminates the specimen with the light having plural wavelengths from a second elevation angle greater than the first elevation angle;
an objective lens which receives light from the specimen illuminated by the first illumination unit and the specimen illuminated by the second illumination unit;
a beam splitter which branches into the light from the specimen illuminated by the first illumination unit and the light from the specimen illuminated by the second illumination unit;
a first detection unit which is set to form a first light from the specimen illuminated by the first illumination unit and detects said first light;
a second detection unit which is set to form a second light from the specimen illuminated by the second illumination unit and detects said second light; and
a signal processing unit which processes signals output from the first detection unit to detect defects in a first area on the specimen, and which processes signals output from the second detection unit to detect defects in a second area on the specimen.

2. The apparatus according to claim 1, wherein said first detection unit and said second detection unit shares a collection optical component which collects light scattered from the specimen illuminated by the first illumination unit and the second illumination unit and a light separator which separates light collected by the collection optical component to a light scattered from the specimen by the illumination of the first illumination unit and a light scattered from the specimen by the illumination of the second illumination unit.

3. The apparatus according to claim 2, wherein, on a surface of the specimen, a fine pattern area and a coarse pattern area are formed, and the signal processing unit processes signals output from the first detection unit to detect defects on the fine pattern area on the specimen and processes signals output from the second detection unit to detect defects on the coarse pattern area on the specimen.

4. The apparatus according to claim 3, wherein said collection optical component having a spacial filter which shades light scattered from fine patterns in the fine pattern area by the illumination of the first illumination unit.

5. The apparatus according to claim 1, wherein said first illumination unit illuminates the specimen with a slit like shaped laser.

6. An apparatus for inspecting a specimen, comprising:
a first illumination unit having a laser source and a first optical component for illuminating a specimen on which patterns are formed with a laser from the laser source at a first elevation angle;
a second illumination unit having a light source and a second optical component for illuminating the specimen with light having plural wavelengths from the light source at a second elevation angle greater than the first elevation angle;
a detection optical unit which collects light scattered from the specimen illuminated by the first illumination unit and the second illumination unit;
a light separator which separates a light scattered from the specimen by the illumination of the first illumination unit from a light scattered from the specimen by the illumination of the second illumination unit;

a first detector which is set to form a first light from the specimen illuminated by the first illumination unit and detects said first light passed through the detection optical unit and the light separator;

a second detector which is set to form a second light from the specimen illuminated by the second illumination unit and detects said second light passed through the detection optical unit and the light separator; and a signal processing unit which processes signals output from the first detector and the second detector to detect defects on the specimen.

7. The apparatus according to the claim 6, wherein, on a surface of the specimen, a fine pattern area and a coarse pattern area are formed, and the signal processing unit processes signals output from the first detector to detect defects on the fine pattern area on the specimen and processes signals output from the second detector to detect defects on the coarse pattern area on the specimen.

8. The apparatus according to claim 7, wherein the first optical component having a beam shape former to form the laser in a slit like shape and illuminate a slit like area on the specimen with the slit like shaped laser.

9. The apparatus according to the claim 7, wherein the detection optical unit having a spacial filter which shades light scattered from fine patterns formed in the fine pattern area by the illumination of the first illumination unit.

10. A method for inspecting a specimen, comprising:

illuminating a specimen on which patterns are formed with a laser from a first elevation angle, via a first illuminator;

illuminating the specimen with a light having plural wavelengths from a second elevation angle greater than the first elevation angle, via a second illuminator;

collecting light from the specimen illuminated by the first illuminator and the specimen illuminated by the second illuminator, via an objective lens;

branching into light from the specimen illuminated by the first illuminator and light from the specimen illuminated by the second illuminator, via a beam splitter detecting light scattered from the specimen illuminated by the laser, via a first detector;

detecting light scattered from the specimen illuminated by the light having plural wavelengths, via a second detector; and processing signals output from the first detector to detect defects in a first area on the specimen and signals output from the second detector to detect defects in a second area on the specimen.

11. The method according to claim 10, wherein the light scattered from the specimen illuminated by the laser and the light scattered from the specimen illuminated by the light having plural wavelengths are both passed through a collection optical component which collects light scattered from the specimen caused by the illumination of the laser and the light having plural wavelengths and are separated with each other by a separator.

12. The method according to claim 11, wherein, on a surface of the specimen, a fine pattern area and a coarse pattern area are formed, the signals output from the first detector are processed to detect defects on the fine pattern area on the specimen, and signals output from the second detector are processed to detect defects on the coarse pattern area on the specimen.

13. The method according to claim 10, wherein during the illumination of the specimen with the laser, the laser is forged in a slit like shape and the specimen is illuminated with the slit like shaped laser.

14. The method according to claim 10, wherein during the detection of light scattered from the specimen illuminated by the laser, the light scattered from the specimen is passed through a spacial filter which shades light scattered from fine patterns formed in the fine pattern area illuminated by the laser.

15. A method for inspecting a specimen, comprising:

illuminating a specimen, on which fine patterns are formed in a fine pattern area and coarse patterns are formed in a coarse pattern area, with a laser from a first incident angle;

illuminating the specimen with a light having plural wavelengths from a second incident angle greater than the first incident angle;

collecting lights scattered from the specimen illuminated by the laser and the light having plural wavelengths;

separating collected lights into a light scattered from the specimen illuminated by the laser and a light scattered from the specimen illuminated by the light having plural wavelengths;

detecting the separated light scattered from the specimen illuminated by the laser with a first detector;

detecting the separated light scattered from the specimen illuminated by the light having plural wavelengths with a second detector;

processing signals output from the first detector and the second detector to detect defects in the fine pattern area and in the coarse pattern area on the specimen, wherein the separated light scattered from the specimen illuminated by the laser is formed by the first detector, and wherein the separated light scattered from the specimen illuminated by the light having plural wavelengths is formed by the second detector.

16. The method according to claim 15, wherein the signals output from the first detector is processed to detect defects in the fine pattern area on the specimen and signals output from the second detector is processed to detect defects in the coarse pattern area on the specimen.

17. The method according to claim 16, wherein, during the detection of the separated light scattered from the specimen illuminated by the laser, the light scattered from the specimen is passed through a spacial filter which shades light scattered from fine patterns formed in the fine pattern area illuminated by the laser.

18. The method according to claim 15, wherein, during the illumination of the specimen with the laser, the specimen is illuminated with a slit like shaped laser.

* * * * *